US009226686B2

(12) United States Patent
Blair

(10) Patent No.: US 9,226,686 B2
(45) Date of Patent: Jan. 5, 2016

(54) METHOD AND APPARATUS TO ACCOUNT FOR TRANSPONDER TAGGED OBJECTS USED DURING MEDICAL PROCEDURES

(75) Inventor: William Blair, San Diego, CA (US)

(73) Assignee: RF Surgical Systems, Inc., Bellevue, WA (US)

( * ) Notice: Subject to any disclaimer, the term of this patent is extended or adjusted under 35 U.S.C. 154(b) by 453 days.

(21) Appl. No.: 12/951,988

(22) Filed: Nov. 22, 2010

(65) Prior Publication Data

US 2011/0181394 A1 Jul. 28, 2011

Related U.S. Application Data

(60) Provisional application No. 61/263,726, filed on Nov. 23, 2009.

(51) Int. Cl.
*H04Q 5/22* (2006.01)
*G08B 13/14* (2006.01)
(Continued)

(52) U.S. Cl.
CPC ............... *A61B 5/062* (2013.01); *A61B 5/7495* (2013.01); *A61B 5/02055* (2013.01)

(58) Field of Classification Search
CPC ........... H04Q 5/22; G08B 13/14; G05B 19/00
USPC ......... 128/899; 340/505, 572.1, 10.34, 568.1; 705/28; 382/224
See application file for complete search history.

(56) References Cited

U.S. PATENT DOCUMENTS 2,740,405 A 4/1956 Riordan
3,031,864 A 5/1962 Freundlich
(Continued)

FOREIGN PATENT DOCUMENTS

AU 199852698 B2 3/1993
AU 2003249257 A1 2/2004
(Continued)

OTHER PUBLICATIONS

Barnes et al., "Design for a FET based 1 MHz, 10kV Pulse Generator," Pulsed Power Conference, Digest of Technical Papers, Tenth IEEE International, 2:1335-1340, 1995.
(Continued)

*Primary Examiner* — Nam V Nguyen
(74) *Attorney, Agent, or Firm* — Seed IP Law Group PLLC

(57) ABSTRACT

Medical procedure related objects (e.g., instruments, supplies) tagged with transponders may be accounted for in a medical procedure environment via a medical object accounting system using a number of antennas, and optional readers. A first set of antennas may be configured to interrogate sterile fields and/or non-sterile fields which do not encompass a body of a patient to account for the objects proximate a start and an end of a medical procedure. Sterile fields may encompass working surfaces of tables and stands, typically used by nurses. Readers (e.g., symbol, RFID) may be employed. A database may be maintained with information including a current status of each instrument or supply, for instance as checked in or checked out. On notification of a discrepancy, a handheld antenna and/or second set of antennas may interrogate a volume encompassing a body of a patient for retained instruments or supplies. The system may be automatically configured (e.g., loading appropriate software) on communicative coupling of a device (e.g., antenna, reader, peripheral device).

32 Claims, 12 Drawing Sheets

(51) Int. Cl.
  *G05B 19/00* (2006.01)
  *A61B 17/00* (2006.01)
  *A61B 5/06* (2006.01)
  *A61B 5/00* (2006.01)
  *A61B 5/0205* (2006.01)

(56) References Cited

U.S. PATENT DOCUMENTS

| | | | |
|---|---|---|---|
| 3,422,816 A | 1/1969 | Robinson et al. |
| 3,587,583 A | 6/1971 | Greenberg |
| D240,166 S | 6/1976 | Cartmell et al. |
| 4,034,297 A | 7/1977 | Giorgi et al. |
| 4,114,601 A | 9/1978 | Abels |
| 4,193,405 A | 3/1980 | Abels |
| 4,422,548 A | 12/1983 | Cheesman et al. |
| D272,943 S | 3/1984 | Stone et al. |
| 4,477,256 A | 10/1984 | Hirsch |
| 4,540,398 A | 9/1985 | Barson et al. |
| 4,626,251 A | 12/1986 | Shen |
| 4,636,208 A | 1/1987 | Rath |
| 4,639,253 A | 1/1987 | Dyer et al. |
| 4,645,499 A | 2/1987 | Rupinskas |
| 4,658,818 A | 4/1987 | Miller, Jr. et al. |
| 4,681,111 A | 7/1987 | Silvian |
| 4,704,109 A | 11/1987 | Rupinskas |
| 4,718,897 A | 1/1988 | Elves |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,966,595 A | 10/1990 | Meringola |
| 4,992,675 A | 2/1991 | Conner, Jr. et al. |
| 5,031,642 A | 7/1991 | Nosek |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,105,829 A | 4/1992 | Fabian et al. |
| 5,107,862 A | 4/1992 | Fabian et al. |
| 5,112,325 A | 5/1992 | Zachry |
| D330,872 S | 11/1992 | Ball |
| 5,181,021 A | 1/1993 | Lee et al. |
| 5,188,126 A | 2/1993 | Fabian et al. |
| 5,190,059 A | 3/1993 | Fabian et al. |
| 5,203,767 A | 4/1993 | Cloyd |
| 5,224,593 A | 7/1993 | Bennett |
| 5,231,273 A | 7/1993 | Caswell et al. |
| 5,235,326 A | 8/1993 | Beigel et al. |
| 5,258,742 A | 11/1993 | Soldevila Domingo et al. |
| 5,329,944 A | 7/1994 | Fabian et al. |
| 5,353,011 A | 10/1994 | Wheeler et al. |
| D353,343 S | 12/1994 | Eberhardt |
| D354,927 S | 1/1995 | Andrau |
| D356,052 S | 3/1995 | Andrau |
| D359,705 S | 6/1995 | Ball |
| 5,446,447 A | 8/1995 | Carney et al. |
| 5,450,622 A | 9/1995 | Vandegraaf |
| 5,456,718 A | 10/1995 | Szymaitis |
| 5,482,036 A | 1/1996 | Diab et al. |
| 5,575,781 A | 11/1996 | DeBusk |
| D378,614 S | 3/1997 | Jensen |
| 5,629,498 A | 5/1997 | Pollock et al. |
| 5,650,596 A | 7/1997 | Morris et al. |
| 5,664,582 A | 9/1997 | Szymaitis |
| D385,037 S | 10/1997 | Jensen |
| 5,725,517 A | 3/1998 | DeBusk |
| 5,767,816 A | 6/1998 | Cosman |
| 5,792,128 A | 8/1998 | DeBusk |
| D412,135 S | 7/1999 | Saito |
| 5,923,001 A | 7/1999 | Morris et al. |
| 5,928,151 A | 7/1999 | Hossack et al. |
| 5,931,824 A | 8/1999 | Stewart et al. |
| 5,963,132 A | 10/1999 | Yoakum |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassøe |
| 6,075,797 A | 6/2000 | Thomas |
| 6,093,869 A | 7/2000 | Roe et al. |
| D429,337 S | 8/2000 | Sanfilippo |
| 6,172,608 B1 | 1/2001 | Cole |
| 6,201,469 B1 | 3/2001 | Balch et al. |
| 6,211,666 B1 | 4/2001 | Acker |
| 6,215,437 B1 | 4/2001 | Schurmann et al. |
| 6,223,137 B1 | 4/2001 | McCay et al. |
| 6,232,878 B1 | 5/2001 | Rubin |
| 6,270,460 B1 | 8/2001 | McCartan et al. |
| 6,276,033 B1 | 8/2001 | Johnson et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,359,562 B2 | 3/2002 | Rubin |
| 6,366,206 B1 | 4/2002 | Ishikawa et al. |
| D456,907 S | 5/2002 | Sanfilippo |
| D457,634 S | 5/2002 | Rouns et al. |
| 6,384,296 B1 | 5/2002 | Roe et al. |
| 6,401,722 B1 | 6/2002 | Krag |
| 6,441,741 B1 | 8/2002 | Yoakum |
| D471,281 S | 3/2003 | Baura et al. |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,240 B2 | 11/2003 | Lee et al. |
| 6,654,629 B2 | 11/2003 | Montegrande |
| 6,696,954 B2 | 2/2004 | Chung |
| 6,722,783 B2 | 4/2004 | Jackson, Sr. |
| 6,734,795 B2 | 5/2004 | Price |
| 6,744,378 B1 | 6/2004 | Tyburski |
| 6,753,783 B2 | 6/2004 | Friedman et al. |
| D495,055 S | 8/2004 | Silber |
| 6,774,800 B2 | 8/2004 | Friedman et al. |
| 6,777,623 B2 | 8/2004 | Ballard |
| 6,778,089 B2 | 8/2004 | Yoakum |
| 6,786,405 B2 | 9/2004 | Wiedenhoefer |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,838,990 B2 | 1/2005 | Dimmer |
| D502,419 S | 3/2005 | Copen |
| 6,861,639 B2 | 3/2005 | Al-Ali |
| 6,861,954 B2 | 3/2005 | Levin |
| 6,879,300 B2 | 4/2005 | Rochelle et al. |
| 6,909,366 B1 | 6/2005 | Marsh et al. |
| D511,004 S | 10/2005 | Masuda |
| D511,384 S | 11/2005 | Masuda |
| 6,977,504 B2 | 12/2005 | Wright et al. |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,037,336 B2 | 5/2006 | Ward |
| D526,586 S | 8/2006 | McCaghren et al. |
| 7,098,793 B2 | 8/2006 | Chung |
| 7,098,866 B2 | 8/2006 | Desjeux et al. |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,245,893 B1 | 7/2007 | Husted et al. |

(56) References Cited

U.S. PATENT DOCUMENTS

| | | |
|---|---|---|
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| D557,421 S | 12/2007 | Fleck et al. |
| D557,423 S | 12/2007 | Chen |
| D558,352 S | 12/2007 | Sanfilippo |
| 7,307,530 B2 | 12/2007 | Fabian et al. |
| 7,307,595 B2 * | 12/2007 | Schantz .............. G01C 21/206 343/718 |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,408,168 B1 | 8/2008 | Aufrichtig et al. |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| D584,414 S | 1/2009 | Lash et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| D590,342 S | 4/2009 | Dávila et al. |
| 7,513,425 B2 | 4/2009 | Chung |
| 7,557,710 B2 * | 7/2009 | Sanchez ............. A61B 19/0248 235/385 |
| D598,110 S | 8/2009 | Phillips et al. |
| D598,114 S | 8/2009 | Cryan |
| 7,617,137 B2 * | 11/2009 | Kreiner ................. A61B 19/44 340/539.12 |
| 7,644,016 B2 | 1/2010 | Nycz et al. |
| 7,696,877 B2 | 4/2010 | Barnes et al. |
| 7,769,422 B2 | 8/2010 | DiSilvestro et al. |
| 7,795,491 B2 | 9/2010 | Stewart et al. |
| 7,817,046 B2 * | 10/2010 | Coveley ............... A61B 5/1113 340/539.12 |
| 7,855,656 B2 | 12/2010 | Maschke |
| 7,876,097 B2 | 1/2011 | Greim |
| 7,898,420 B2 | 3/2011 | Blair et al. |
| 8,082,192 B2 | 12/2011 | Nycz et al. |
| 8,111,162 B2 | 2/2012 | Barnes et al. |
| 8,169,304 B2 * | 5/2012 | Schuman, Sr. ......... G08B 5/222 340/286.07 |
| 8,193,938 B2 | 6/2012 | Halberthal et al. |
| 8,259,518 B2 | 9/2012 | Peng et al. |
| 8,371,448 B1 | 2/2013 | Reaux |
| 8,454,613 B2 | 6/2013 | Tethrake et al. |
| 8,477,076 B1 | 7/2013 | Nero, Jr. et al. |
| 8,477,077 B1 | 7/2013 | Nero, Jr. et al. |
| 8,780,660 B2 | 7/2014 | Peng |
| 8,872,662 B2 | 10/2014 | Halberthal et al. |
| 8,985,446 B2 | 3/2015 | Fleck et al. |
| 8,994,358 B2 | 3/2015 | McElhinny et al. |
| 2001/0000659 A1 * | 5/2001 | Hayashi et al. ............ 340/10.34 |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0067263 A1 * | 6/2002 | Tafoya ................. G06K 17/00 340/572.1 |
| 2002/0070863 A1 | 6/2002 | Brooking |
| 2002/0143320 A1 | 10/2002 | Levin |
| 2002/0165587 A1 | 11/2002 | Zhang et al. |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2003/0199624 A1 | 10/2003 | Yadav et al. |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. |
| 2004/0254420 A1 | 12/2004 | Ward |
| 2005/0049564 A1 | 3/2005 | Fabian |
| 2005/0110640 A1 | 5/2005 | Chung |
| 2005/0131397 A1 | 6/2005 | Levin |
| 2005/0154293 A1 | 7/2005 | Gisselberg et al. |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0047238 A1 | 3/2006 | Galdenzi et al. |
| 2006/0055537 A1 | 3/2006 | Jackson |
| 2006/0084934 A1 | 4/2006 | Frank |
| 2006/0106368 A1 | 5/2006 | Miller et al. |
| 2006/0109086 A1 | 5/2006 | Amtmann |
| 2006/0187044 A1 * | 8/2006 | Fabian et al. .............. 340/572.1 |
| 2006/0194899 A1 | 8/2006 | Ohashi et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0244652 A1 | 11/2006 | Tethrake et al. |
| 2006/0270933 A1 | 11/2006 | Benson et al. |
| 2007/0004994 A1 | 1/2007 | Sherman |
| 2007/0005141 A1 | 1/2007 | Sherman |
| 2007/0034670 A1 | 2/2007 | Racenet et al. |
| 2007/0038233 A1 | 2/2007 | Martinez et al. |
| 2007/0055109 A1 | 3/2007 | Bass et al. |
| 2007/0109099 A1 | 5/2007 | Raphaeli et al. |
| 2007/0112649 A1 * | 5/2007 | Schlabach ....................... 705/28 |
| 2007/0125392 A1 * | 6/2007 | Olson et al. .................. 128/899 |
| 2007/0152823 A1 | 7/2007 | Hirahara et al. |
| 2007/0209957 A1 | 9/2007 | Glenn et al. |
| 2007/0216062 A1 | 9/2007 | Frank |
| 2007/0216526 A1 * | 9/2007 | Volpi et al. .................... 340/505 |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0244470 A1 | 10/2007 | Barker, Jr. et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0007411 A1 * | 1/2008 | Levin .......................... 340/572.1 |
| 2008/0021308 A1 | 1/2008 | Dimmer et al. |
| 2008/0024277 A1 | 1/2008 | Volpi et al. |
| 2008/0030303 A1 | 2/2008 | Kobren et al. |
| 2008/0051746 A1 | 2/2008 | Shen-Gunther |
| 2008/0126122 A1 | 5/2008 | Warner et al. |
| 2008/0132860 A1 | 6/2008 | Smith et al. |
| 2008/0204245 A1 | 8/2008 | Blair et al. |
| 2008/0231452 A1 | 9/2008 | Levin |
| 2008/0237341 A1 | 10/2008 | Fleck et al. |
| 2008/0243404 A1 | 10/2008 | Banhegyesi |
| 2008/0272913 A1 | 11/2008 | Barnes et al. |
| 2008/0281190 A1 | 11/2008 | Petcavich et al. |
| 2008/0296573 A1 | 12/2008 | Zmood et al. |
| 2009/0014518 A1 | 1/2009 | Stewart et al. |
| 2009/0267765 A1 * | 10/2009 | Greene et al. .............. 340/568.1 |
| 2009/0309734 A1 * | 12/2009 | Jayaprakash .......... G06Q 10/08 340/572.1 |
| 2009/0315681 A1 | 12/2009 | Blair |
| 2009/0317002 A1 * | 12/2009 | Dein ............................ 382/224 |
| 2010/0033309 A1 | 2/2010 | Blair |
| 2010/0108079 A1 | 5/2010 | Blair |
| 2010/0109848 A1 | 5/2010 | Blair et al. |
| 2011/0050411 A1 * | 3/2011 | Schuman ............... G08B 21/22 340/539.13 |
| 2011/0130636 A1 * | 6/2011 | Daniel ................. G08B 25/016 |

(56) References Cited

U.S. PATENT DOCUMENTS

| | | | 600/301 |
|---|---|---|---|
| 2011/0277359 A1 | 11/2011 | Halberthal et al. | |
| 2012/0031547 A1 | 2/2012 | Halberthal et al. | |
| 2012/0139706 A1 | 6/2012 | Nero, Jr. et al. | |
| 2013/0199720 A1 | 8/2013 | Halberthal et al. | |
| 2014/0068915 A1 | 3/2014 | Halberthal et al. | |

FOREIGN PATENT DOCUMENTS

| CN | 101460096 A | 6/2009 |
|---|---|---|
| EP | 1 612 554 A1 | 1/2006 |
| EP | 2 087 850 A2 | 8/2009 |
| JP | 2009539478 A | 11/2009 |
| WO | 02/39917 A1 | 5/2002 |
| WO | 2004/008387 A1 | 1/2004 |
| WO | 2004/086997 A1 | 10/2004 |
| WO | 2006/060781 A1 | 6/2006 |
| WO | 2007/146091 A1 | 12/2007 |
| WO | 2008/024921 A1 | 2/2008 |
| WO | 2008/106552 A1 | 9/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |

OTHER PUBLICATIONS

Clearcount Medical Solutions, "The SmartSponge System," Downloaded from http://clearcount.com on Oct. 20, 2009, 7 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

International Search Report, mailed Jan. 4, 2010, for PCT/US2009/045312, 3 pages.

Written Opinion, mailed Jan. 4, 2010, for PCT/US2009/045312, 3 pages.

Blair et al., "Tag and Detection Device," U.S. Appl. No. 60/458,222, filed Mar. 27, 2003, 23 pages.

Blair et al., "Improved Apparatus and Method for Detecting Objects Using Tags and Wideband Detection Device," U.S. Appl. No. 60/811,376, filed Jun. 6, 2006, 16 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Transponder Housing and Device to Mark Implements, Such As Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Barnes et al., "Method, Apparatus and Article for Detection of Transponder Tagged Objects, for Example During Surgery," U.S. Appl. No. 61/056,787, filed May 28, 2008, 60 pages.

Blair, "Transponder Device to Mark Implements, Such As Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair, "Multi-Modal Transponder and Method and Apparatus to Detect Same," U.S. Appl. No. 61/102,749, filed Oct. 3, 2008, 48 pages.

Blair et al., "Method and Apparatus to Detect Transponder Tagged Objects, for Example During Surgery," U.S. Appl. No. 61/109,104, filed Oct. 28, 2008, 73 pages.

Blair, "Detectable Surgical Objects and Methods of Making Same," U.S. Appl. No. 61/109,142, filed Oct. 28, 2008, 47 pages.

Blair et al., "Method and Apparatus to Detect Transponder Tagged Objects, for Example During Medical Procedures," U.S. Appl. No. 61/242,704, filed Sep. 15, 2009, 127 pages.

Blair, "Transponder Device to Mark Implements, Such As Surgical Implements, and Method of Manufacturing and Using Same," U.S. Appl. No. 61/220,452, filed Jun. 25, 2009, 46 pages.

Blair, "Radio Opaque Device with Resonant Nanostructures," U.S. Appl. No. 61/163,813, filed Mar. 26, 2009, 47 pages.

Blair et al., "Method and Apparatus to Detect Transponder Tagged Objects, for Example During Surgery," U.S. Appl. No. 61/222,443, filed Jul. 1, 2009, 95 pages.

Blair, "Transponder Device to Mark Implements, Such As Surgical Implements, and Method of Manufacturing and Using Same," U.S. Appl. No. 61/224,323, filed Jul. 9, 2009, 57 pages.

Blair et al., "Method and Apparatus to Detect Transponder Tagged Objects and to Communicate with Medical Telemetry Devices, for Example During Medical Procedures," U.S. Appl. No. 61/242,699, filed Sep. 15, 2009, 158 pages.

Blair, "Method and Apparatus to Account for Transponder Tagged Objects Used During Medical Procedures," U.S. Appl. No. 61/263,726, filed Nov. 23, 2009, 78 pages.

Blair, "Transponder Housing," Design U.S. Appl. No. 29/322,539, filed Aug. 6, 2008, 6 pages.

Blair, "Attachment Article to Attach a Transponder to a Surgical Sponge," Design U.S. Appl. No. 29/336,007, filed Apr. 27, 2009, 4 pages.

Blair, "Attachment Article to Attach a Transponder to a Surgical Sponge," Design U.S. Appl. No. 29/336,008, filed Apr. 27, 2009, 7 pages.

Blair, "Article to Attach a Transponder to a Surgical Sponge," Design U.S. Appl. No. 29/336,009, filed Apr. 27, 2009, 4 pages.

Blair et al., "Method and Apparatus to Detect Transponder Tagged Objects and to Communicate With Medical Telemetry Devices, for Example During Surgery," U.S. Appl. No. 61/222,847, filed Jul. 2, 2009, 122 pages.

\* cited by examiner

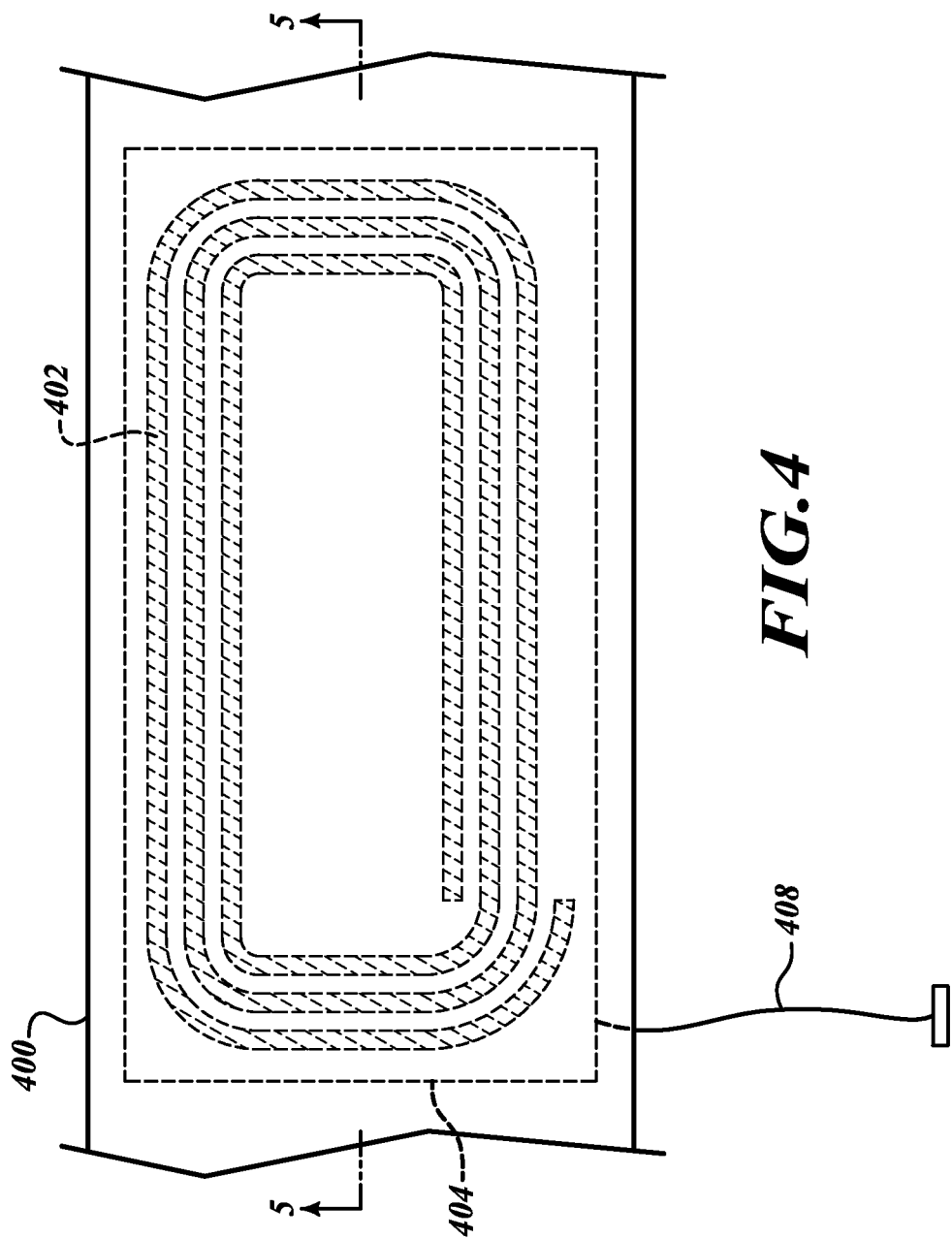

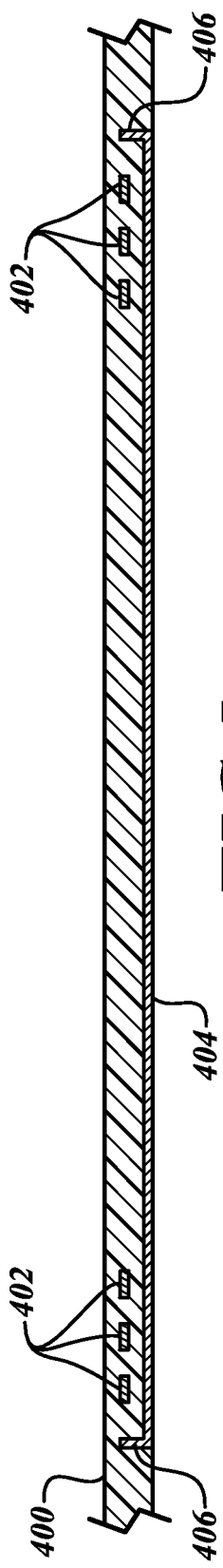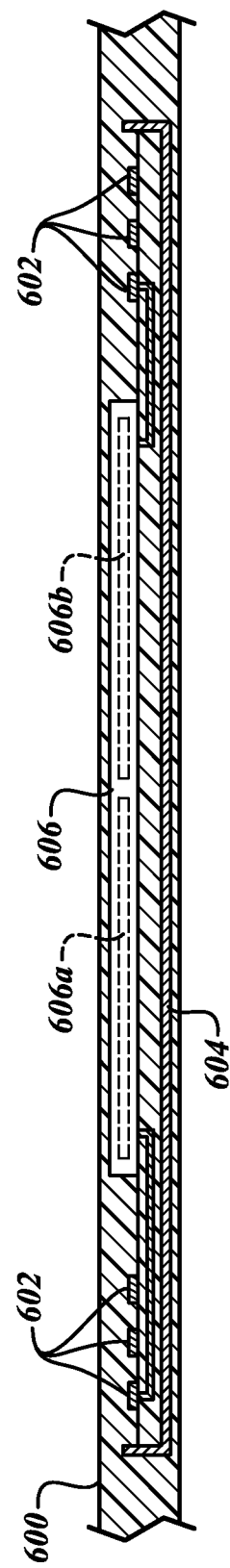

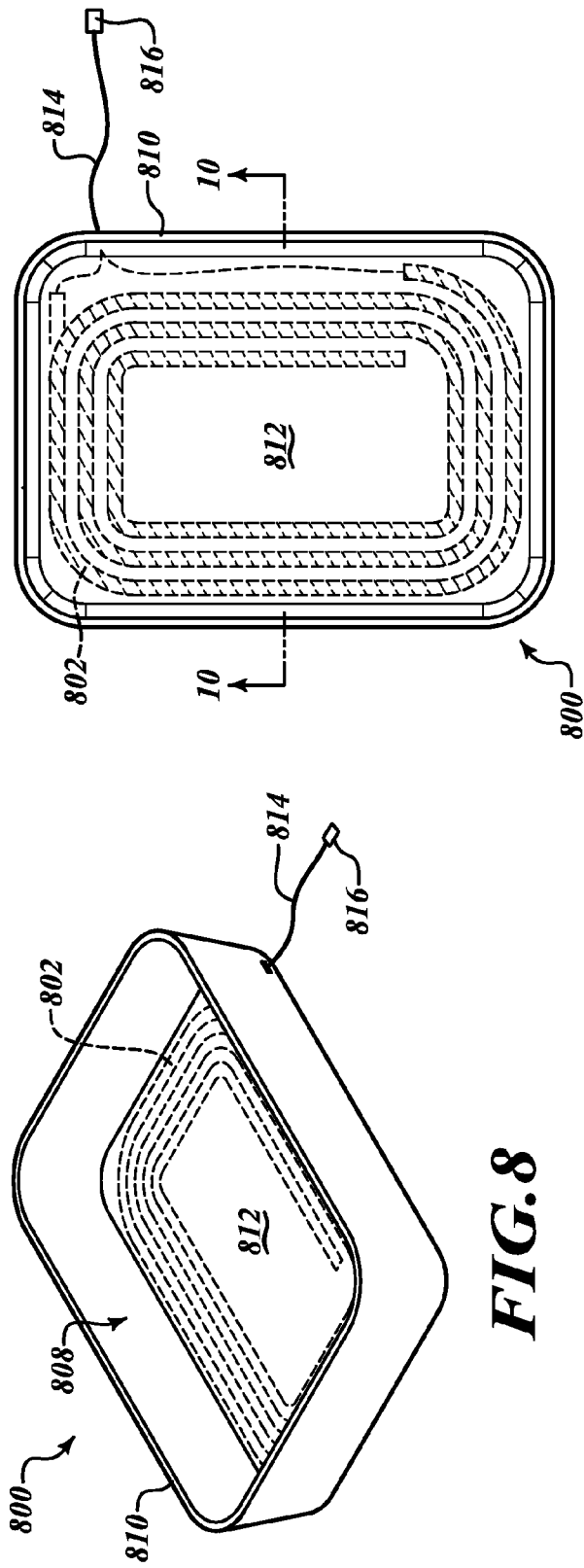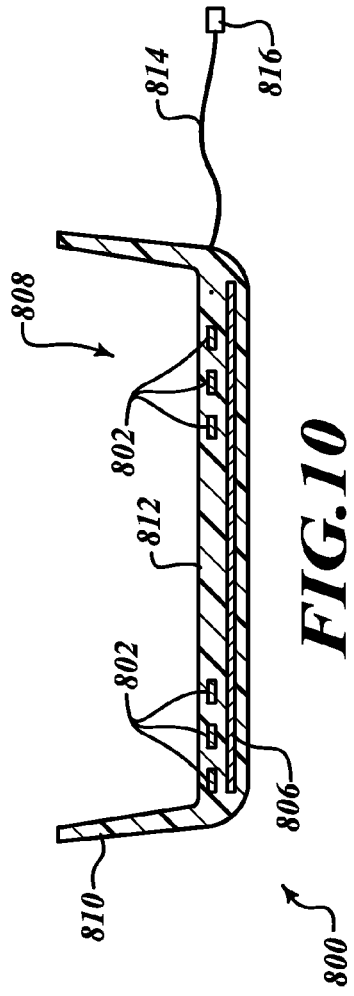

METHOD AND APPARATUS TO ACCOUNT FOR TRANSPONDER TAGGED OBJECTS USED DURING MEDICAL PROCEDURES

CROSS REFERENCE TO RELATED APPLICATIONS

This application claims benefit under 35 U.S.C. 119(e) to U.S. provisional patent application Ser. No. 61/263,726 filed Nov. 23, 2009 which is incorporated herein by reference in its entirety.

BACKGROUND

1. Technical Field

The present disclosure generally relates to a wireless medical procedure environment, and more particularly accounting for transponder tagged medical procedure objects such as instruments and supplies in an environment in which medical procedures are performed.

2. Description of the Related Art

It is important to determine whether objects associated with a medical procedure, for instance surgery or child birth delivery, are present in a patient's body before completion of the medical procedure. Such objects may take a variety of forms used in medical procedures. For example, the objects may take the form of instruments, for instance scalpels, scissors, forceps, hemostats, and/or clamps. Also for example, the objects may take the form of related accessories and/or disposable objects, for instance surgical sponges, gauzes, and/or absorbent pads. When used in surgery, failure to locate an object before closing the patient may require additional surgery, and in some instances may have serious adverse medical consequences. In other medical procedures, such as vaginal child birth deliveries, failure to remove objects, for instance gauze or absorbent pads can lead to infections.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Consequently, a new approach to prevention of foreign object retention in medical procedure environments is highly desirable.

BRIEF SUMMARY

A method of accounting for medical procedure objects may be summarized as including: at least proximate a start of a medical procedure on a patient, automatically detecting each of a number of medical procedure objects for performing the medical procedure within at least one sterile field which at least one sterile field is at least proximate to the patient but which at least one sterile filed does not encompass any portion of a body of the patient; and at least proximate an end of the medical procedure on the patient, automatically determining whether each of the number of medical procedure objects detected within the at least one sterile field at least proximate the start of the medical procedure are present in at least one of either the at least one sterile field or at least one non-sterile field, neither of which the at least one sterile field or the at least one non-sterile field encompass any portion of the body of the patient.

The method may further include: in response to determining that a discrepancy exists between the number of medical procedure objects present in the at least one sterile field at least proximate the start of the medical procedure and the number of medical procedure objects present in the at least one sterile field or the at least one non-sterile field at least proximate the end of the medical procedure, providing an indication indicative of the existence of the discrepancy. Providing an indication indicative of the existence of the discrepancy may include at least one of providing an aural indication, providing a visual indication or providing a tactile indication. Automatically detecting each of a number of medical procedure objects within at least one sterile field may include at least one of wirelessly reading information from each of the medical procedure objects present in the at least one sterile field or wirelessly counting each of the medical procedure objects present in the at least one sterile field, and wirelessly reading or wirelessly counting may include at least one of optically imaging, optically scanning, or wirelessly interrogating at least one of the medical procedure objects or a number of transponders associated with the medical procedure objects. The at least one sterile field may be respectively coextensive with at least a portion of at least one of a back table, a supply table, or an instrument table, and automatically detecting each of a number of medical procedure objects within at least one sterile field may include detecting any of the medical procedure objects present within respective portion of the back table, the supply table, or the instrument table. The at least one sterile field may be respectively coextensive with an outer perimeter of an instrument tray, and automatically detecting each of a number of medical procedure objects within at least one sterile field may include detecting any of the medical procedure objects present within the outer perimeter of the instrument tray. The at least one non-sterile field may include a waste receptacle and automatically determining whether each of the number of medical procedure objects detected within the at least one sterile field at least proximate the start of the medical procedure are present in at least one of either the at least one sterile field or at least one non-sterile field may include determining whether any of the medical procedures objects are within a respective confines of the waste receptacle. The method may further include: each time one of the medical procedure objects is removed from the at least one sterile field, identifying the removed medical procedure object as checked out in a database; and each time the medical procedure object is returned to the at least one sterile field or to the at least one non-sterile field, identifying the returned medical procedure object as checked-in in the database. The method may further include: providing an indication indicative if one of the medical procedure objects is returned to the at least one sterile field after being present in the at least one non-sterile field. The method may further include: between the start and the end of the medical procedure on the patient, automatically tracking the presence or an absence of each of the number of medical procedure object within the at least one sterile field or the at least one non-sterile field.

A system to account for medical procedure objects may be summarized as including: a plurality of sterile fields, each of the sterile fields encompassing an area that excludes any portion of a body of a patient on which a medical procedure is performed; a control subsystem including at least one processor and at least one processor-readable storage medium, the control subsystem configured to: at least proximate a start of a medical procedure on a patient, automatically detect each of a number of medical procedure objects for performing the medical procedure within any of the sterile fields; and at least proximate an end of the medical procedure on the patient, automatically determine whether each of the number of medical procedure objects detected within any of the sterile fields at least proximate the start of the medical procedure are present in at least one of either the sterile fields or at least one non-sterile field.

The system may further include at least one receiver; and a plurality of antennas communicatively coupled to the at least one receiver, the antennas and receiver providing a range that is about coextensive with the sterile fields and which range does not extend into any portion of the body of the patient when the patient is supported by a patient support structure during the medical procedure. The system may further include at least one transmitter communicatively coupled to the antennas to transmit an interrogation signal to any transponders in the sterile fields. The sterile fields may be coextensive with at least a portion of a back table, a supply table, and an instrument table, respectively. One of the sterile fields may be coextensive with a portable instrument tray and at least one of the antennas may be physically coupled to the portable instrument tray. The system may include a plurality of substrates, each of the substrates carrying at least a respective one of the antennas, the substrates positionable with respect to a respective one of each of the sterile fields such that a range of the at least respective one of the antennas covers the respective sterile field. The at least one receiver may include a plurality of receivers, each of at least some of the receivers physically coupled to a respective one of the substrates. The at least one receiver may include a plurality of receivers, each of at least some of the receivers physically housed in a controller console, at least some of the antennas remotely located from the control console and communicatively coupled to respective ones of the receivers via a respective wired connection. At least one of the antennas may be a part of a handheld wand capable of transmitting interrogation signals and receiving response signals in a random orientation. The control subsystem may be further configured to cause interrogations signals to be transmitted and to read identifiers encoded in response signals received from transponders in response to the interrogation signals. The control subsystem may be further configured to: each time one of the medical procedure objects is removed from the at least one sterile field, identify the removed medical procedure object as checked out in a database; and each time the medical procedure object is returned to the at least one sterile field or to the at least one non-sterile field, identify the returned medical procedure object as checked-in in the database. The system may further include: a plurality of antennas communicatively coupled via at least one universal serial bus communications link to the control subsystem, at least some of the antennas located at least proximate respective ones of the sterile fields. The control subsystem may be resident in a console and may be configured by an application program loaded in response to communicative coupling of a reader to the console. The system may further include: a plurality of readers communicatively coupled to the console and positioned at least proximate respective ones of the sterile fields and the non-sterile field, the readers including at least one of radio frequency identification readers or machine-readable symbol readers. The system may further include: at least one cover sized to completely cover at least one of the antennas, the cover comprising a material that is capable of withstanding sterilization.

A system to account for medical procedure objects may be summarized as including: a computer system including at least one processor and at least one computer-readable storage medium; and a number of readers to monitor a number of sterile fields in which at least one of medical implements or medical supplies are kept for use during medical procedures, and which any single one of the sterile fields does not encompass a patient support surface that supports a patient during a medical procedure, the readers selectively communicatively coupleable to the computer system, and wherein a set of instructions are loaded to the at least one computer-readable storage medium in response to an initial communicative coupling of one of the readers to the computer system, the instructions executable by the at least one processor to cause the computer system to check the medical implements and medical supplies into and out of the sterile fields.

The readers may each include a substrate that is positioned at least proximate at least one of a back table, a supply table, or an instrument table. The readers may each include an antenna operable to transmit an interrogation signal to a respective one of the sterile fields and to receive a response signal from any transponders in the respective one of the sterile fields. The readers may be communicatively coupled to the computer system by at least one wired or wireless universal serial bus.

A method of operating a medical procedure object accounting system may be summarized as including: detecting by a computer system an initial communicative coupling of an initial reader; loading a first set of instructions to at least one computer-readable storage medium in response to the detection of an initial communicative coupling of the initial reader to the computer system, the instructions executable by at least one processor of the computer system to cause the computer system to check the medical implements and medical supplies into and out of the sterile fields; and executing the first set of instructions by the at least one processor.

Executing the first set of instructions by the at least one processor may cause the at least one processor to check the medical implements and medical supplies into and out of the sterile fields, by: at least proximate a start of a medical procedure on a patient, automatically detecting any of the medical procedure objects within at least one sterile field which at least one sterile field is at least proximate to the patient but which at least one sterile filed does not encompass any portion of a body of the patient; and at least proximate an end of the medical procedure on the patient, automatically determining whether each of the number of medical procedure objects detected within the at least one sterile field at least proximate the start of the medical procedure are present in at least one of either the at least one sterile field or at least one non-sterile field, neither of which the at least one sterile field or the at least one non-sterile field encompass any portion of the body of the patient. Executing the first set of instructions by the at least one processor may cause the at least one processor to check the medical implements and medical supplies into and out of the sterile fields, by: updating a database stored in the at least one computer-readable medium to reflect a status of a medical procedure object. The method may further include:

detecting by a computer system an initial communicative coupling of a non-reader; loading a second set of instructions to at least one computer-readable storage medium in response to the detection of an initial communicative coupling of the initial reader to the computer system, the instructions executable by at least one processor of the computer system to cause the computer system to processor information collected by the non-reader; and executing the second set of instructions by the at least one processor.

A transponder may be summarized as including at least one antenna, a power supply circuit and a memory circuit communicatively coupled to the antenna where the memory circuit is gamma ray and heat resistant.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 4 is a top plan view of a mat that houses at least one antenna and RF shield, according to one illustrated embodiment, the mat positionable on a table or stand to interrogate wireless RFID transponders carried by the medical procedure instruments and supplies.

FIG. 5 is a cross-sectional view of the mat of FIG. 4 taken along section line 5-5.

FIG. 6 is a cross-sectional view of a mat with an integral wireless RFID reader, according to another illustrated embodiment.

FIG. 8 is an isometric view of a tray that includes at least one antenna, according to one illustrated embodiment.

FIG. 9 is a top plan view of the tray of FIG. 8.

FIG. 10 is a cross-sectional view of the tray of FIG. 8 taken along section line 10-10, showing an RF shield in the tray.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
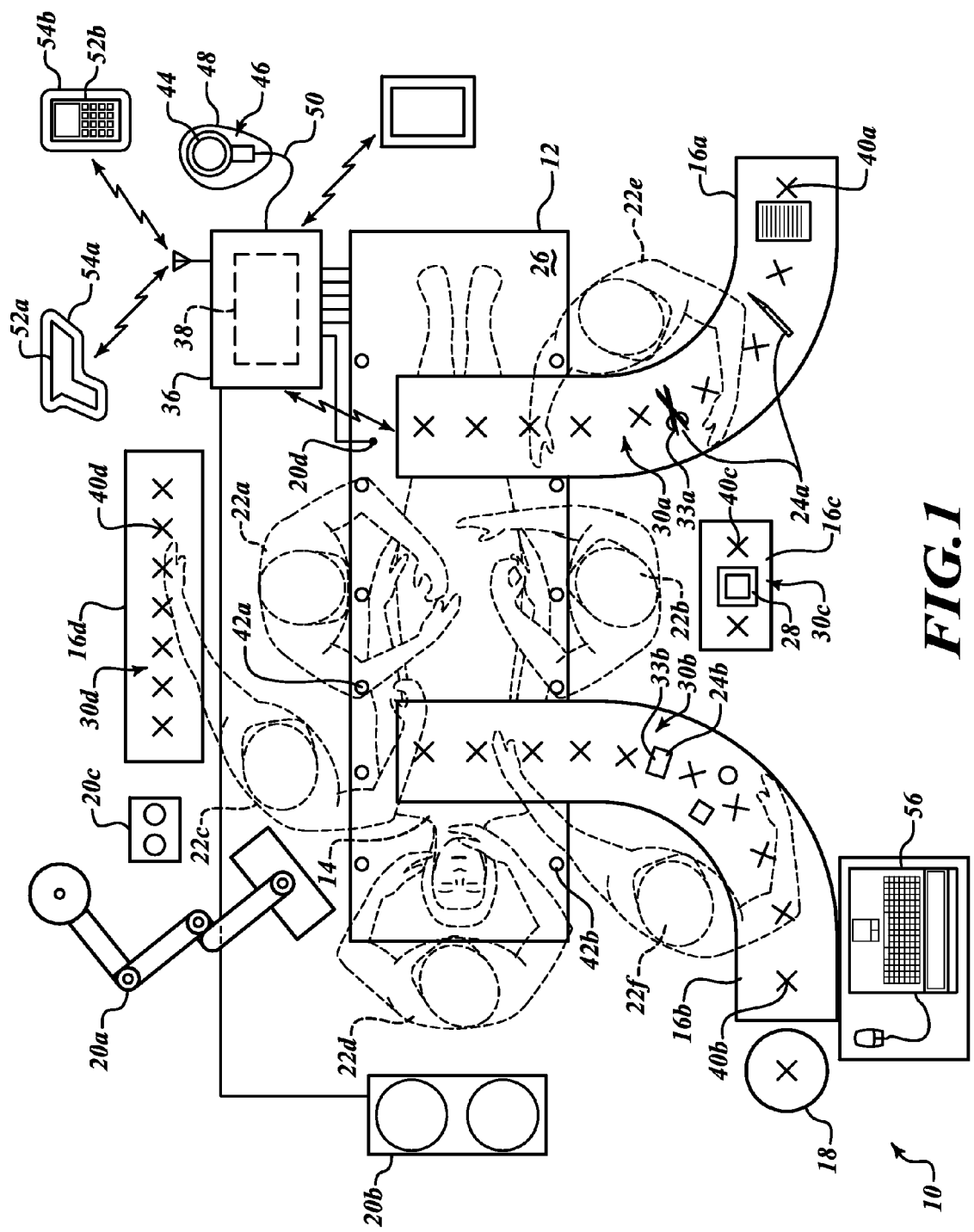
FIG. 1 is a top plan view of an environment in which a medical procedure is performed and which includes a patient support structure to support at least a portion of a patient, a number of tables or stands on which medical procedure instruments and supplies are carried, a number of pieces of medical procedure equipment, a number of medical care providers, and a system to monitor or track the medical procedure instruments or supplies which are tagged with transponders, according to one illustrated embodiment.

FIG. 1 shows a medical procedure environment 10 in which medical procedures are performed, in the form of a surgical environment or operating room in which surgeries are performed. Other medical procedure environments may take the form of a patient room in which child birth deliveries or other medical procedures are performed, and examination room or a physician's office, etc.

The medical procedure environment 10 typically includes a patient support structure 12 which can carry a patient 14 or portion thereof. The medical procedure environment 10 typically includes a number of tables or stands (collectively 16) for holding medical procedure related instruments or implements and/or supplies, collectively referred to herein and in the claims as medical procedure objects. For instance, the medical procedure environment 10 may include one or more instrument tables 16a, supply tables 16b, Mayo stands or tables 16c and/or back tables 16d. The medical procedure environment 10 may include one or more receptacles 18, for example to collect used supplies. Additionally, the medical procedure environment will typically include one or more pieces of medical procedure related equipment (collectively 20), for instance one or more lamps 20a, anesthetizing equipment 20b, heart/lung machines or cardiopulmonary bypass machines, ventilators, cauterization equipment, defibrillator 20c, aspirator equipment, infusion pump, dialysis machine, intra-aortic balloon pump, various monitors such as blood pressure, heart or pulse rate, pulse-oxygen (pulse-ox or pulse oximetry) sensor 20d, temperature, EKG sensors or electrodes or electrical conductivity sensors, intra-cranial pressure sensors, pH sensors, other dedicated medical diagnostic, therapeutic or monitoring equipment, etc.

Where the medical procedure environment 10 is an operating room or operating theater, there will typically be a number of medical providers present. For instance, medical providers present during a surgery may include a surgeon 22a, a first assistant surgeon 22b, a second assistant surgeon 22c, an anesthetist 22d, an instrument nurse 22e, a supply nurse 22f, and/or one or more circulating nurses (not illustrated). The surgeons 22a-22c are typically responsible for working directly on the patient 14, for example cutting, excising, cauterizing, suturing, ablating, fastening, etc. The anesthetist 22d is typically responsible for administering anesthesia and monitoring certain vital signs, such as blood pressure, pulse, oxygen level and/or blood gases. The instrument and supply nurses 22e, 22f, respectively, may be responsible for handing instruments 24a and supplies 24b from the instrument and supply tables 16a, 16b to the surgeons 22a-22c, and collecting the instruments 24a and supplies 24b after use. As a non-limiting example, instruments 24a may take the form of scalpels, scissors, forceps, hemostats, and/or clamps. Supplies 24 may take the form of disposable or reusable supplies, and as a non-limiting example, may take the form of sponges (e.g., surgical sponges), gauze and/or padding.

The patient support structure 12 may take the form of a table (e.g., operating table), bed or other structure which may include a patient support surface 26 and a pedestal or base (not shown) which supports the patient support surface 26. The patient support surface 26 should have dimensions sufficient to support at least a portion of a patient 14 during a medical procedure, for instance during surgery. Hence, the patient support surface 26 may have a length of six feet or more and a width of two feet or more. The patient support surface 26 may have two or more articulated sections (not shown), or may be an unarticulated or unitary structure as illustrated. Hinges or other coupling structures may couple any articulated sections. For instance, hinges may be located along a longitudinal axis of the patient support surface 26 at locations that would approximate the anticipated position of a between a patient's legs and torso and between the patient's torso and head.

The patient support surface 26 is preferably made of a rigid material and is preferably radiolucent allowing radiological imaging (e.g., X-rays, CAT scans, MRIs). Various radiolucent materials may be employed, for instance carbon fiber or radiolucent plastics (e.g., resin impregnated carbon fiber). Such advantageously allows radiological technologies to be employed, for example X-ray imaging. For example, the patient support surface 26 may be molded from plastics such as an acrylic or a phenolic resin (e.g., commercially available under the trademark SPAULDITE®). In some embodiments, the patient support structure 26 may include a frame. The frame may be made of a metal which may not be radiolucent. In such embodiments, the frame preferably makes up a small percentage of the total area of the patient support surface 26. The patient support surface 26 may be capable of withstanding multiple cycles of sterilization (e.g., chemical, heat, radiation, etc.). A large variety of surgical tables, patient beds and other structures capable of supporting or carrying a patient or a portion of a patient are commercially available. Many of these commercially available structures include electric motors and electronics. Typically, there is no or minimum regulation of non-ionizing electromagnetic radiation generated by such electric motors and electronics. Hence, many medical procedure environments 10 in which medical procedures are performed tend to be electromagnetically noisy environments.

The patient support structure 12 may include one or more film receiving receptacles (not shown). The film receiving receptacles may be spaced relatively below a patient support surface 26 of the patient support structure 12. The film receiving receptacles are sized, dimensioned and/or positioned to receive film, for example X-ray film. The film receiving receptacles may be sized and/or dimensioned to receive a film tray or other film holder (not illustrated) which holds the film. Along with the use of radiolucent materials, such advantageously allows a patient X-ray images or other radiological images of the patient to be produced, generated or made, while the patient is supported by the patient support structure 26. As used herein an in the claims, the term radiolucent means substantially transmissive to energy in the X-ray portion of the electromagnetic spectrum, that is passing sufficient X-ray energy to produce an X-ray image at standard power levels and standard conditions employed in conventional medical imaging.

The patient support structure 12 may include one or more mattresses or pads (not illustrated), and/or may include one or more sheets (not illustrated). The mattresses or pads may take a variety of forms, and may be disposable, or may be capable of withstanding multiple cycles of sterilization (e.g., chemical, heat, radiation, etc.). The mattresses or pads are preferably radiolucent (e.g., interior of cotton or a foam material such as a closed or an open cell foam rubber or LATEX®, liquid or a gas, exterior of cotton, nylon, rayon or other natural or synthetic materials). The mattresses or pads may take a conventional form, for example cotton, open cell or a closed cell foam rubber, with or without an appropriate cover. Alternatively, the mattresses or pads may include one or more bladders (e.g., dual layer urethane envelope) to receive a fluid (e.g., air, water, etc.) to selectively inflate one or more portions of the mattresses or pads, and/or to control a temperature of one or more portions of the mattresses or pads. In such embodiments, the fluid should be radiolucent. The mattresses or pads may be detachably secured to the patient support structure 12 via various fasteners, for instance ties, or hook and loop fastener commonly available under the trademark VELCRO®.

The pedestal or base may be fixed, or may be moveable. The pedestal or base may include one or more actuators (e.g., motors, pumps, hydraulics, etc.) and/or drive mechanisms (e.g., gears, mechanical couplings) or linkages (not shown) that allow a position and/or orientation of the patient support surface 26 to be adjusted. For example, the pedestal or base may telescope to allow the patient support surface 26 to be mechanically raised and lowered. Also for example, the pedestal or base may allow the patient support surface 26 to be mechanically tilted or rotated about an axis that is perpendicular to the patient support structure 12.

The instrument table, supply table, Mayo stand or table, back table 16 may take a variety of forms. The table(s) or stand(s) 16 may include a generally planer surface, which may be supported by legs, or supported by brackets attached to a fixed structure such as a wall. Some tables or stands 16 may include a recess or opening, for example to receive a bucket or tray. The table(s) or stand(s) 16 are typically made of a metal, for instance a stainless steel. One or more of the table(s) or stand(s) 16 may be moveable, for example including wheels or coasters. One or more of the table(s) or stand(s) 16 may be fixed. The instrument 16*a* and supply tables 16*b* may have an arcuate shape, such as illustrated in FIG. 1. A portion of the instrument 16*a* and supply tables 16*b* may extend over the patient support structure 12, and hence the patient 14, when in use. The arcuate shape may advantageously maximize the useable area of the table 16*a*, 16*b* that can be reached by the instrument or supply nurse 22*e*, 22*f* with minimal amount of movement. Often the table or stand 16 will be covered by one or more sterile drapes. In addition to carrying instruments 24*a*, supplies 24*b*, the tables or stands 16 may carry any other object including medical procedure related equipment, trays 28, buckets, implants, etc.

One or more receptacle(s) 18 may receive used medical instruments or supplies, such as used sponges or gauze, and hence may be denominated as waste receptacles. The receptacle(s) 18 may take a variety of forms, for example buckets. Such receptacle(s) 18 may be open, or may have a cover that is selectively positionable between open and closed positions. Such receptacle(s) 18 may have a variety of shapes and sizes, and may be made of any number of materials, including but not limited to metals and plastics. The receptacle(s) 18 may include a disposable liner. The receptacle(s) 18 may, for example, include wheels or coasters to allow easy movement thereof, or may omit such.

The medical procedure environment 10 includes a number of sterile fields 30*a*-30*d* (collectively 30). These sterile fields 30 include areas or volumes which have been sterilized or created under sterile conditions and hence are considered to be substantially free of microorganisms. As illustrated in FIG. 1, these sterile fields 30*a*-30*d* may be coextensive with the surfaces of the instrument table 16*a*, supply table 16*b*, Mayo stand or table 16*c*, back table 16*d*, respectively.

The medical procedure environment may have additional or other sterile fields. For example, the patient 14 or portions thereof may constitute one or more sterile fields, although certain embodiments discussed below a concerned with sterile fields that do not encompass portions of the body of a patient 14. The medical procedure environment may also include a number of non-sterile fields 32. Non-sterile fields 32 are areas or volumes which are not considered to be substantially free of microorganisms, whether or not such fields actually contain microorganisms. In the illustrated embodiment, the waste receptacle 18 is identified as being a non-sterile field 32, although is some situations even waste receptacles may be treated as sterile fields or may actually be substantially free of microorganisms even though treated as a non-sterile field.

The medical procedure environment 10 may include a medical procedure object accounting system 34 used to account for the presence of absence of medical procedure objects such as instruments and supplies used in performing medical procedures. As discussed in detail below, the medical procedure object accounting system 34 is operable to ascertain the presence or absence of medical procedure related objects (e.g., instruments 24*a*, supplies 24*b*) which are tagged with transponders 33*a*, 33*b* (collectively 33).

The medical procedure object accounting system 34 includes a console 36 which includes a control subsystem 38. As discussed in detail below, the control subsystem 38 will typically include a processor and computer- or processor-readable storage medium (e.g., memory), and be configured to account for medical procedure objects used in performing a medical procedure.

The medical procedure object accounting system 34 also includes a first number of antennas 40*a*-40*d* (collectively 40, illustrated as crosses, only one called out for each table or stand 16) positioned to monitor one or more sterile fields and/or non-sterile fields without monitoring any portion of the patient 14. The medical procedure object accounting system 34 may optionally include a second number of antennas 42*a*, 42*b* (collectively 42, illustrated as circles, only two called out), which are positioned to monitor volumes that include portions of the body of the patient 14. For example, the antennas 42 may be carried by the patient support surface 12, for example on an outer surface thereof or internally therein. The antennas 42 may be incorporated into the patient support surface in any manner taught in U.S. patent application Ser. No. 12/606,688, filed Oct. 27, 2009 or in U.S. patent application Ser. No. 12/606,963, filed Oct. 27, 2009, both of which are incorporated herein by reference in their entireties. The antennas 40, 42 are communicatively coupleable to the control subsystem 38 by one or more wired or wireless communication paths, for example coaxial cable.

The antennas 40, 42 may take a variety of forms, for example coil antennas, dipole antennas, slot antennas. Portions of one or more of the antennas 40, 42 may overlap. For example, where the antennas 40, 42 are coil antennas, each formed of one or more coils, a portion of an area enclosed by an outermost coil of each antenna may overlap a portion of an area enclosed by an outermost coil of a neighboring antenna. In such embodiments, neighboring antennas 40, 42 may be electrically insulated from one another by one or more electrically insulating layers or substrates. For example, successively adjacent antennas 40, 42 may be carried one opposite surfaces (e.g., opposed outer surfaces, or multiple inner surfaces, or one or more outer and inner surfaces) of a single substrate. As discussed in more detail below, the antennas 40, 42 may advantageously be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) to be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

The medical procedure object accounting system 34 may optionally include one or more handheld antennas 44. While illustrated as a loop antenna, the handheld antenna 44 may take other forms. The handheld antenna 44 may be incorporated or integrated into a wand 46. Such may allow scanning of the body of a patient 14 should an accounting discrepancy occur. One or more disposable covers 48 may be employed to avoid having to sterilize the wand 46 between operations or patients 14. The handheld antenna 44 is communicatively coupled to the control subsystem 38 by a wired or wireless communications path, for example via a coaxial cable 50 or other communication path.

One of the medical personnel 22 may wave the wand 46 over the patient 14 on the patient support surface 26. In one embodiment, the handheld antenna 44 emits interrogation signals to excite any transponder 33 which may be in or near the patient 14, and receives any response signals emitted by the transponder(s) 33 if present. In another embodiment, the handheld antenna 44 emits interrogation signals to excite any transponder 33 which may be in or near the patient 14, and the antennas 42 carried by the patient support structure 12 receives any response signals emitted by the transponder(s) 33 if present. In yet another embodiment, the antennas 42 carried by the patient support structure 12 emit interrogation signals to excite any transponder 33 which may be in or near the patient 14, and the handheld antenna 44 receives any response signals emitted by the transponder(s) 33 if present. In some embodiments, the handheld antenna 44 may interact (e.g., inductively) with other antennas 42 to, for example, advantageously increase sensitivity and/or range. For example, an electromagnetic field may be set up between the handheld antenna 44 and one or more of the antennas 42, and disturbances of the electromagnetic field caused by the presence of a transponder 33 therein detected. Other approaches that combined the handheld antenna 44 and one or more of the antennas 42 may be advantageously employed.

The medical procedure object accounting system 34 may optionally include one or more handheld readers 52a, 52b (collectively 52, only two illustrated). The handheld readers 52 may take a variety of forms. For example, one or more of the handheld readers 52a may take the form of a machine-readable symbol reader such as a scanner or imager configured to read information encoded in machine readable symbols such as barcode symbols, area or matrix code symbols or stacked code symbols. The machine-readable symbols typically encode identifying information, for instance a unique identifier. Additionally, or alternatively, one or more of the handheld readers 52b may take the form of a radio frequency identification (RFID) reader, such as in RFID interrogator configured to transmit interrogation signals to RFID transponders 33 and receive responses to the interrogation signals from the RFID transponders 33. Such responses typically encode identifying information, for instance a unique identifier. Details of such are discussed in U.S. patent application Ser. No. 12/472,199 filed May 26, 2009, as well as in U.S. provisional patent application Ser. Nos. 61/056,299 and 61/102,749, filed May 27, 2008 and Oct. 3, 2008, respectively, and which are incorporated by reference herein in their entireties. Some RFID readers are also configured to write or store information to RFID transponders 33 capable of such. Suitable automatic data collection readers 52a, 52b may be commercially available from Intermec Technologies or Symbol Technologies. Additionally, or alternatively, automatic data collection readers may be capable of reading or writing to other data carriers such as optical memories, touch memories (e.g., available from Dallas Semiconductor), magnetic stripes, etc. The automatic data collection readers 54a, 54b may be employed to read information from data carriers physically associated with various objects (e.g., instruments 24a, supplies 24b (e.g., sponges, pads, gauze, articles and/or other supplies), medical equipment 20, and/or the patient 14 and/or one or more medical care providers (e.g., doctors, nurses, anesthesiologist, radiology technician) 22, for instance from a data carrier of a wrist band, anklet or badge worn by the patient 14 or medical care provider 22.

The readers 52 are communicatively coupled to the control subsystem 38 by a wired (e.g., coaxial cable) or wireless (e.g., radio) communications path. Such readers 52 may allow reading identifiers from various medical procedure objects, for example by reading a respective machine-readable symbol and/or RFID transponder attached to the medical procedure object. For instance, the automatic data collection readers 54a, 54b may be employed to read information from data carriers physically associated with various objects (e.g., instruments 24a, supplies 24b (e.g., sponges, pads, gauze, articles and/or other supplies), medical equipment 20, and/or the patient 14 and/or one or more medical care providers (e.g., doctors, nurses, anesthesiologist, radiology technician) 22, for instance from a data carrier of a wrist band, anklet or badge worn by the patient 14 or medical care provider 22. The control subsystem 38 may employ such information in accounting for presence, absence or location of the various medical procedure objects. One or more disposable covers 54a, 54b may be employed to avoid having to sterilize the readers 52 between operations or patients 14.

The RFID transponders 33 may be attached to hemostats, scissors, certain forms of forceps, and the like. In some embodiments, the transponders 33 may be coupled to the instrument 24a or supply 24b by way of a clamp or holder. In some embodiments, the transponders 33 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 33 may be attached to the instrument 24a or supply 24b by way of pouches fashioned of sheet material (e.g., surgical fabric) surrounding the transponder 33. The transponder 33 is retained within the pouch, and in some embodiments the pouch may be sewn or otherwise sealed. Sealing may be done with adhesive, hot glue, clamping, grommeting, or the like. Various embodiments of suitable transponders and retention devices are discussed in U.S. Provisional Patent Application No. 60/811,376 filed Jun. 6, 2006, U.S. Provisional Patent Application No. 61/091,667 filed Aug. 25, 2008, U.S. patent application Ser. No. 11/759,141 filed Jun. 6, 2007, U.S. patent application Ser. No. 12/046,396 filed Mar. 11, 2008, U.S. Pat. No. 6,026,818 issued Feb. 22, 2000, U.S. Design patent application Ser. No. 29/322,539 filed Aug. 6, 2008 and U.S. Design Pat. No. D568,186 issued May 6, 2008, all of which are incorporated herein by reference in their entireties.

Some embodiments may employ pulsed wide band frequency hopping with dynamic adjustment of the transmission frequency in the various frequency bands and the use of switched capacitors to achieve such, which may permit the use of inexpensive transponders which are not accurately tuned to a chosen or selected resonant frequency. In some embodiments, some antennas 40, 42, 44 and readers 52b may be used to read information from RFID transponders, while in other embodiments some antennas 40, 42, 44 may be used to interrogate resonant transponders that do not store identifiers or have any storage medium. Typically, the first plurality of antennas 40 will be used to interrogate RFID transponders to determine respective identifiers for each.

Information received from the RFID transponder, read from machine-readable symbols or from other data carriers may, for example, include an identifier, such as a unique identifier that uniquely identifies the data carrier (e.g., RFID transponder or tag, machine-readable symbol, magnetic stripe). A database stored on a computer-readable medium may associate the identifier with information that identifies the medical procedure related object (e.g., instruments and/or supplies used in performing medical procedures) to which the data carrier is attached, as well as information about the medical procedure related object. The information may include identity of the medical procedure related object such as manufacturer, model, type, classification, lot number and/or date of manufacture. The information may include a history of the object, for instance number of uses, number and/or type of sterilization cycles, number and/or date of refurbishment, dates and/or times of use, dates of inspection and/or identity of inspector. The information may be accessible (e.g., read, write) by the control subsystem 38 of the medical procedure object accounting system 34, and/or by one or more readers 52 associated with the medical procedure object accounting system 34.

The medical procedure environment 10 may optionally include a computer system, for instance a circulator computer system 56. Such may be a standard general purpose computer, such as a PC computer, that executes suitable software. Such may communicate with the control subsystem 38 of the medical procedure object accounting system 34 to exchange data and/or instructions. The circulator computer system 56 may, for example, be used to off load data collected by the medical procedure object accounting system 34. Such a circulator computer system 56 may be any conventional computer system employed in medical environments such as operating rooms or theaters.

Figure 2:
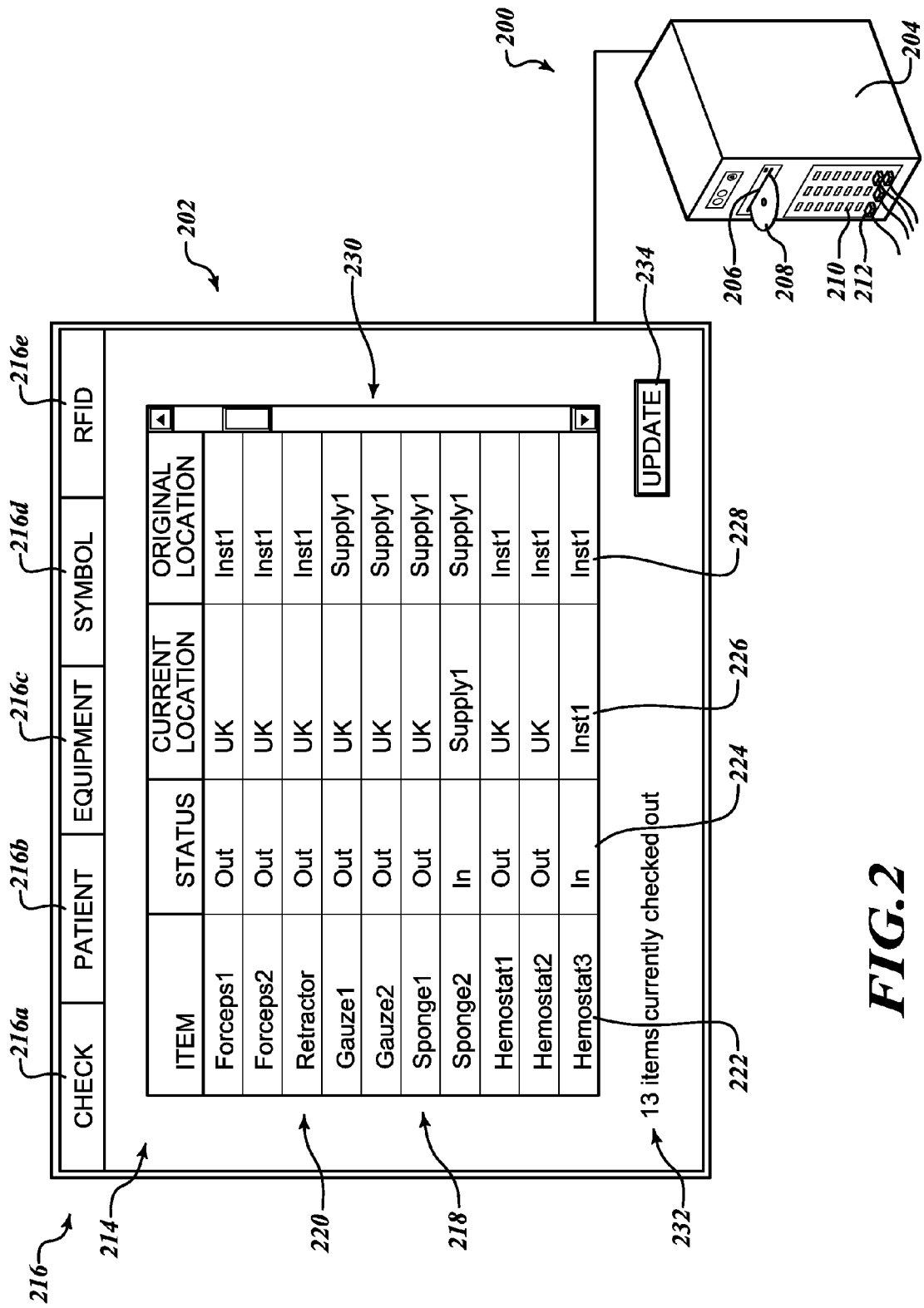
FIG. 2 a front elevational view of a console and display of the system of FIG. 1 showing the plurality of antennas, according to one illustrated embodiment.

FIG. 2 shows a console 200 and display 202 of a medical procedure object accounting system 34, according to one illustrated embodiment.

The console 200 may include a housing 204 which houses the control subsystem 38 (FIG. 1). The console 200 may include one or more slots 206 or other receptacles to receive computer- or processor readable media 208, for instance spinning media (e.g., compact disks, floppy disks), fixed media (e.g., Flash cards). The console 200 may also include one or more ports or connectors 210 (only one called out in FIG. 2) to allow selective connection and disconnection of various devices to the control subsystem of the console 200. The connection may provide communications and/or power between the console 200 and various connected devices. Devices may take a variety of forms, for instance antennas 40, 42 (FIG. 1), medical equipment 20 (FIG. 1) and any other device capable of transmitting or receiving data and/or instructions or capable of any other form of communications. Such ports or connectors 210 may take the form of various industry standard ports or connectors, for example Universal Serial Bus ports. While illustrated as physical ports to couple with a connector or plug 212 (only one called out in FIG. 2), the ports 210 may take the form of one or more wireless transmitters, receivers or transceivers. Such may, for instance be compatible with various industry standards, for instance 802.11b, 802.11c, 802.11n, or BLUETOOTH®.

The display 202 may be any screen or monitor suitable to display information and/or a user interface (e.g., graphical user interface). The display 202 may, for example take the form of an LCD display panel or a CRT display. The display 202 may be a stand alone, separate piece of equipment. Alternatively, the display 202 may be integrated into the housing 204 of the console 200.

The display 202 is communicatively coupled to the control subsystem 38 (FIG. 1). The control subsystem 38 (FIG. 1) is configured to control the images displayed on the display 202. The display 202 may provide all, or a portion, of a user interface, for an end user to interact with the control subsystem 38. Thus, the display 202 may take the form of a touch panel display, allowing an end user to enter commands or instructions, or otherwise make selections, via a graphical user interface 214. Alternatively, or additionally, one or more other user input devices may be provided, for instance a keyboard, keypad, mouse, trackball, other pointer control device, or a microphone and voice activated interface.

The graphical user interface 214 may include one or more menus 216. The menus 216 may include icons 216a-216e corresponding to specific functions or operational modes which may be selected. A specific function or mode may be selected by touching the appropriate portion of the user interface or placement of a cursor over the appropriate portion of the user interface. In response, a set of related icons may be displayed for instance by way of a pull-down menu or dialog box. Such may allow further selections or configuration of the specific mode or function. Icons 216a-216e for some exemplary functions or operational modes are illustrated. Selection of a checking function or mode 216a causes the medical procedure object accounting system 34 to check medical procedure related instruments and supplies in and out in a database. Selection of a patient function or mode icon 216b may allow patient specific information to be viewed and/or recorded or modified. Selection of an equipment function or mode 216c may allow the end user to read information or data produced or collected by various pieces of medical equipment on the display 202, for instance, blood pressure, heart rate, temperature, blood oxygen levels, respiration, electrocardiogram, etc. The equipment function or mode may additionally, or alternatively, allow an end user to configure parameters of a piece of medical equipment via the user interface. Selection of the symbol reading function or mode icon 216d may allow use of a machine-readable symbol reader 52a, while the selection of the RFID reading function or mode icon 216e may allow the use of an RFID reader 52b (FIG. 1).

The graphical user interface 214 may one or more windows or panels 218 (only one illustrated) that present or display information. Multiple windows or panels 218 may be displayed at the same time, or individual windows or panels 218 may be displayed one by one, for example in response to a user selection of a particular function or mode or selection of a particular window or panel 218.

The illustrated window or panel 218 is related to a medical procedure related object accounting mode or function that checks medical procedure related instruments and supplies in and out in a database stored in at least one computer- or processor-readable storage medium, hence is also denominated as a checking mode or function.

In the accounting or checking mode or function, the medical procedure object accounting system 34 determines which medical procedure related instruments 24a and supplies 24b are present in one or more sterile fields 30 prior to or at the start of a medical procedure. The medical procedure object accounting system 34 also determines which medical procedure related instruments 24a and supplies 24b are present in one or more sterile fields 30 and/or non-sterile fields just prior to or at the end of the medical procedure. The medical procedure object accounting system 34 may optionally determine which medical procedure related instruments 24a and supplies 24b are present in one or more sterile fields 30 and/or non-sterile fields during the medical procedure, for example from time-to-time, periodically or even continuously. The medical procedure object accounting system 34 may make such determinations by, for example transmitting interrogation signals from the first plurality of antennas 40, to excite, power or otherwise cause transponders 33 (FIG. 1) that are not in the body of the patient 14 (FIG. 1) to transmit or emit a response signal. One or more antennas 40, 42 may receive the response signals from the excited or powered transponders 33. The medical procedure object accounting system 34 may decode the received response signals to determine identifying information encoded therein. The medical procedure object accounting system 34 may catalog the medical procedure related instruments 24a and supplies 24b that are present based on the identifying information. For example, the response signals may contain unique identifiers stored or hardcoded into the transponders. These unique identifiers may be mapped to information about the respective instruments 24a and/or supplies 24b, for instance in a database. Alternatively, information about the respective instruments 24a and/or supplies 24b may be stored in the transponder and encoded in the response signals. Such information may include the name or identity of the instrument 24a or supply 24b, a manufacturer identification, model identification, date put in use, date refurbished or sharpened, date sterilized, method of sterilization, history of use, etc.

The medical procedure object accounting system 34 may display information related to the status of the various instruments 24a and/or supplies 24b in a chart 218 or other format. For example, the chart 218 may include an entry, for instance a row 220 (only one called out in FIG. 2), for each instrument 24a and supply 24b present proximate a start of the medical procedure. The instrument 24a or supply 24b may be identified by an identifier 222, for instance a commonly recognized name or description. A current status of the instrument 24a or supply 24b may be identified by an appropriate indicator 224 (e.g., In/Out, Present/Absent). Optionally, a current location of the instrument 24a or supply 24b may be identified by an appropriate indicator 226 (e.g., instrument table, supply tables, Mayo stand, back table, or unknown). Optionally, an original or starting location of the instrument 24a or supply 24b may be identified by an appropriate indicator 228 (e.g., instrument table, supply tables, Mayo stand, back table, or unknown). A scroll bar 230 of similar graphical user interface tool may be provided to allow a user to review information for a large number of instruments 24a and supplies 24b.

The medical procedure object accounting system 34 may determine if there is a discrepancy between the medical procedure related objects that were present in areas other than the body of the patient at the start and at the end of the medical procedure. The medical procedure object accounting system 34 may provide a suitable warning or notification 232 if a discrepancy exists, and/or if a discrepancy does not exist. While illustrated as a visual notification, an aural and/or tactile notification may additionally or alternatively be supplied.

The graphical user interface 214 may include one or more icons 234 (only on illustrated), user selection of which may cause certain actions. For instance, selection of an update icon 234 may cause the medical procedure object accounting system 34 to rescan or re-interrogate the sterile and/or non-sterile fields to account for the presence, absence or location of various medical procedure related instruments 24a and tools 24b.

Figure 3:
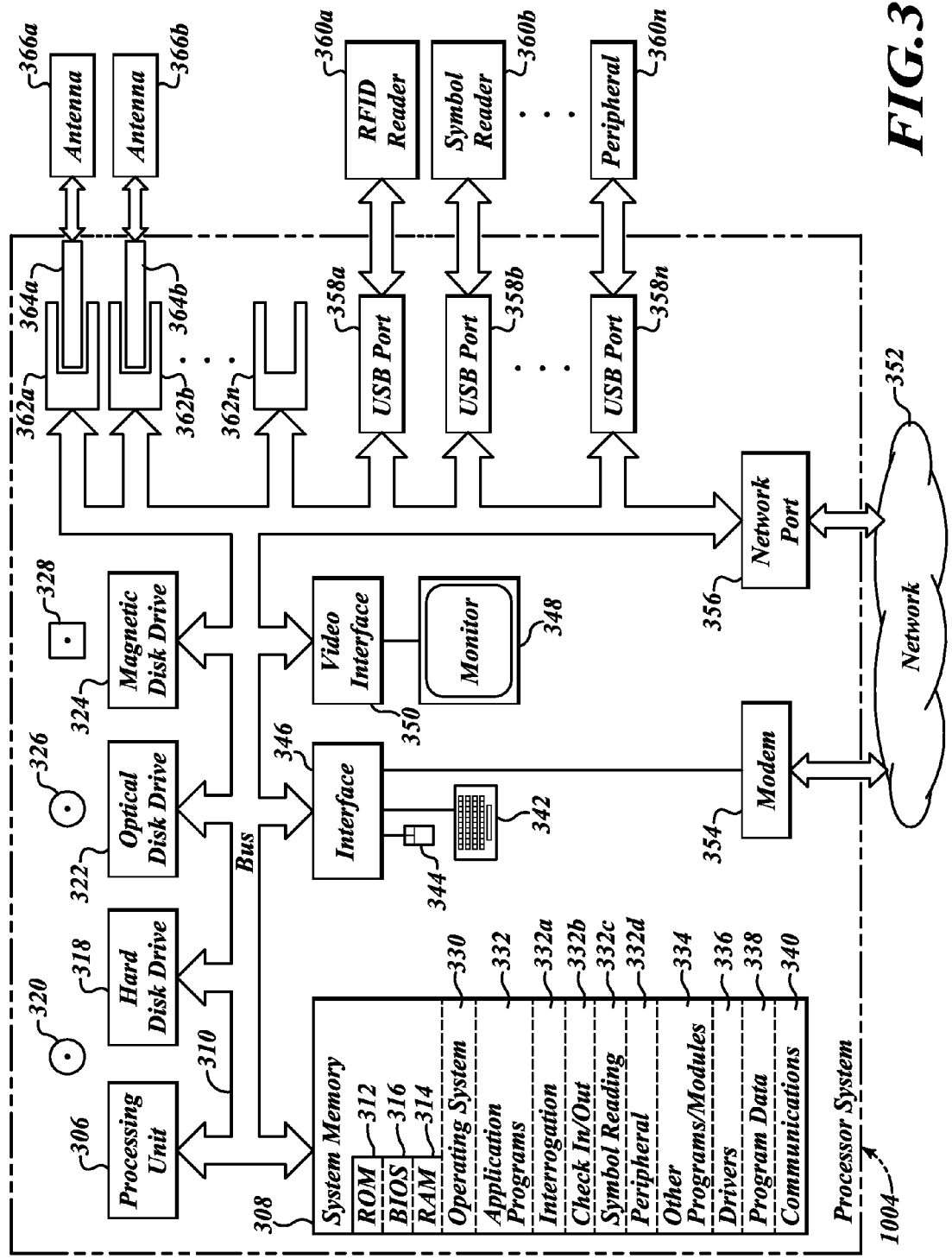
FIG. 3 is schematic diagram of a control subsystem according to one illustrated embodiment, control subsystem including a processor system, plug-in boards and various ports to provide communications with antennas, readers and various non-reader peripheral devices or equipment.

FIG. 3 and the following discussion provide a brief, general description of a suitable processor system 304 in which the various illustrated embodiments, as well as other embodiment can be implemented. Although not required, some portion of the embodiments will be described in the general context of computer-executable instructions or logic, such as program application modules, objects, functions, procedures or macros being executed by a computer or processor. Those skilled in the relevant art will appreciate that the illustrated embodiments as well as other embodiments can be practiced with other computer or processor based system configurations, including handheld devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processor based devices, which are linked through a communications network. In a distributed computing environment, program modules may be located in local and/or remote memory storage devices.

The processor system 304 may take the form of a conventional personnel computer (PC), which includes one or more processors 306, system memories 308 and system buses 310 that couple various system components including the system memory 308 to the processor 306. The processor system 304 and its components will at times be referred to in the singular herein, but this is not intended to limit the embodiments to a single system or single components, since in certain embodiments, there will be more than one system or other networked computing device or multiple instances of any component involved. Unless described otherwise, the construction and operation of the various blocks shown in FIG. 3 are of conventional design. As a result, such blocks need not be described in further detail herein, as they will be understood by those skilled in the relevant art.

The processor 306 may be any logic processor, such as one or more central processor units (CPUs), microprocessors, digital signal processors (DSPs), application-specific integrated circuits (ASICs), field programmable gate arrays (FPGAs), etc.

As described in applicant's prior applications, the processor 306 may take the form of a soft processor core, such as that supplied by XILINX under the name MICROBLAZE™ which implements a 32-bit processor including memory caches and a floating point unit. A soft core processor is one that is implemented by interconnected FPGA logic cells instead of by a traditional processor logic. The processor core may be connected to the internal FPGA peripherals using a 32-bit processor bus called the On-Chip Peripheral Bus. The XILINX supplied peripherals for the MICROBLAZE™ processor core include external memory interfaces, timers, and general purpose I/O. Custom logic to create the transmit signals, sample the ADC, and accumulate the transponder return signals may be designed as a peripheral to the soft processor core. The custom logic may be part of the design of the FPGA.

Alternatively, the processor 306 may take the form of a full microprocessor. Non-limiting examples of commercially available microprocessors include, but are not limited to, an 80×86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. For example, the processor 306 may take the form of a full microprocessor such as the ATOM™ processor, commercially available from Intel Corporation. The full microprocessor may be communicatively coupled to multiple analog antenna channels, for example via one or more plug-in boards 364a, 364b (collectively 364, only two shown) which carry respective FPGAs and one or more suitable buses. The FPGA may, for example, act as a co-processor and/or cache. For example, the plug-in boards 364 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which patent applications are incorporated herein by reference in its entirety.

The system bus 310 can employ any known bus structures or architectures, including a memory bus with memory controller, a peripheral bus, and a local bus. A relatively high bandwidth bus architecture may be employed. For example, a PCI Express™ or PCIe™ bus architecture may be employed, rather than an ISA bus architecture. Suitable FPGAs may include those from ATMEL Corporation. Such FPGAs may advantageously have built in PCIe bus architecture, allowing easy integration. This approach may enable more I/O ports, such as USB ports, may provide more or better video options, and may provide faster data rates from the analog antenna channels than otherwise possible using the ISA bus architecture and a soft processor core approach. Some embodiments may employ separate buses for data, instructions and power.

The system memory 308 includes read-only memory ("ROM") 312 and random access memory ("RAM") 314. A basic input/output system ("BIOS") 316, which can form part of the ROM 312, contains basic routines that help transfer information between elements within the processor system 304, such as during start-up.

The processor system 304 also includes a hard disk drive 318 for reading from and writing to a hard disk 320, and an optical disk drive 322 and a magnetic disk drive 324 for reading from and writing to removable optical disks 326 and magnetic disks 328, respectively. The optical disk 326 can be a CD or a DVD, etc., while the magnetic disk 328 can be a magnetic floppy disk or diskette. The hard disk drive 318, optical disk drive 322 and magnetic disk drive 324 communicate with the processor 306 via the system bus 310. The hard disk drive 318, optical disk drive 322 and magnetic disk drive 324 may include interfaces or controllers (not shown) coupled between such drives and the system bus 310, as is known by those skilled in the relevant art. The drives 318, 322, 324, and their associated computer-readable media 320, 326, 328, provide nonvolatile storage of computer-readable instructions, data structures, program modules and other data for the processor system 304. Although the depicted processor system 304 employs hard disk 320, optical disk 326 and magnetic disk 328, those skilled in the relevant art will appreciate that other types of computer-readable media that can store data accessible by a computer may be employed, such as magnetic cassettes, flash memory cards, Bernoulli cartridges, RAMs, ROMs, smart cards, etc.

Program modules can be stored in the system memory 308, such as an operating system 330, one or more application programs 332, other programs or modules 334, drivers 336 and program data 338.

The application programs 332 may, for example, include interrogation logic 332a, check in/out logic 332b, and machine-readable symbol reading logic 332c, as well as another other peripheral logic 332d associated with operating a non-reader device, referred to in FIG. 3 and elsewhere herein as peripheral logic and peripheral device, respectively. The logic 332a-332d may, for example, be stored as one or more executable instructions. The interrogation logic 332a may include logic or instructions to cause antennas and/or RFID interrogator to transmit wireless interrogation signals, receive response signals to the interrogations signals and decode information encoded in the response signals, for instance unique identifiers stored in RFID transponders. Such may encode information in the interrogation signals, for instance information to be encoded in an RFID transponder. The check in/out logic 332b may include logic to monitor or track a status of various medical procedure instruments and supplies. Such may, for example, update information in a database stored on one or more computer- or processor-readable storage media. Such may also allow the generation of queries and retrieval of information from such database. Such may, for example, update create a record or field in the database for each medical procedure instrument or supply that is present in a sterile field before or at the start of a medical procedure. Such may also, for example, update a respective record or field of the database if a medical procedure instrument or supply is removed from a particular sterile field. Such may also, for example, update a respective record or field of the database if the medical instrument or supply is returned to a sterile field, returned to a different sterile field or returned to a non-sterile field. Such may take the form of identifying a particular instrument as being checked in if detected in some sterile or non-sterile field, and otherwise identifying the particular instrument as checked out. A query may be run, either from time-to-time or before ending a medical procedure to ensure that all the medical instruments and supplies present at the start of the medical procedure are present and accounted for at the end of the medical procedure. This ensures that no medical instruments or supplies are left behind in a body of a patient undergoing a medical procedure where the sterile and non-sterile fields do not encompass any portion of the body of the patient. The machine-readable symbol reading logic 332c may allow the capture and decoding of information encoded in machine-readable symbols, such as barcode symbols, area or matrix code symbols and/or stacked code symbols. Such logic is commonly found in dedicated machine-readable symbol readers. The peripheral logic 332d can be any logic loaded into or otherwise stored in a computer- or processor-readable storage medium. The peripheral logic 332d allows operation of a peripheral device, such as a non-reader type device. For instance, the peripheral logic 332d may collect data from one or more pieces of medical procedure equipment (e.g., cautery equipment, heart-lung machine, ablation system, anesthesia deliver apparatus) or medical procedure sensors (e.g., electrode, pulse-oximetry sensor, blood pressure sensor, temperature probe, heart monitor). Interrogation logic 332a, machine-readable symbol reading logic 332c, and/or peripheral logic 332d may be automatically loaded into one or more computer- or processor-readable storage medium in response to the communicative coupling of a respective device to the console 36. Such may advantageously provide plug and play functionality for a wide variety of devices.

The system memory 308 may also include communications programs 340, for example a server and/or a Web client or browser for permitting the processor system 304 to access and exchange data with other systems such as user computing systems, Web sites on the Internet, corporate intranets, extranets, or other networks as described below. The communications programs 340 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 3 as being stored in the system memory 308, the operating system 330, application programs 332, other programs/modules 334, drivers 336, program data 338 and server and/or browser 340 can be stored on the hard disk 320 of the hard disk drive 318, the optical disk 326 of the optical disk drive 322 and/or the magnetic disk 328 of the magnetic disk drive 324. A user can enter commands and information into the processor system 304 through input devices such as a touch screen or keyboard 342 and/or a pointing device such as a mouse 344. Other input devices can include a microphone, joystick, game pad, tablet, scanner, biometric scanning device, etc. These and other input devices are connected to the processor 306 through an interface 346 such as a universal serial bus ("USB") interface that couples to the system bus 310, although other interfaces such as a parallel port, a game port or a wireless interface or a serial port may be used. A monitor 348 or other display device is coupled to the system bus 310 via a video interface 350, such as a video adapter. Although not shown, the processor system 304 can include other output devices, such as speakers, printers, etc.

The processor system 304 operates in a networked environment using one or more of the logical connections to communicate with one or more remote computers, servers and/or devices via one or more communications channels, for example, one or more networks 352. These logical connections may facilitate any known method of permitting computers to communicate, such as through one or more LANs and/or WANs, such as the Internet, intranet and/or extranet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a WAN networking environment, the processor system 304 may include a modem 354 for establishing communications over a WAN, for instance the Internet. The modem 354 is shown in FIG. 3 as communicatively linked between the interface 346 and the network 352. Additionally or alternatively, another device, such as a network port 356, that is communicatively linked to the system bus 310, may be used for establishing communications over the network 352.

One or more interfaces or ports 358a-358n (collectively 358, only three illustrated) that are communicatively linked to the system bus 310, may be used for establishing communications over a WAN, LAN, parallel or serial cable. In some embodiments, the interfaces or ports 358 may take the form of USB ports allowing communication via respective USB cables. Such may allow a variety of equipment to communicate with the processor system 304. For example, such may allow communicative coupling with one or more RFID interrogators or readers 360a, machine-readable symbol readers 360b (e.g., machine-readable symbol scanners or imagers), and peripheral equipment 360n (collectively 360, only three illustrated). The readers 360a, 360b may be configured to transmit pre-processed information to the processor system 304, for instance identifiers read from RFID transponders or optical symbols (e.g., printed or inscribed markings). The processor system 304 may be configured to use such information. For instance, the processor system 304 may be configured to check medical procedure instruments and supplies in and out in the database based on identifiers reader by the readers 360a, 360b. Additionally, or alternatively, the processor system 304 may be configured to control or otherwise send instructions and/or data to the readers 360a, 360b. Likewise, the processor system 304 may be configured to check medical procedure instruments and supplies in and out in the database based on information received from the peripheral equipment 360c. Additionally, or alternatively, the processor system 304 may be configured to control or otherwise send instructions and/or data to the peripheral equipment 360c.

One or more interfaces or slot connectors 362a-362n (collectively 362, only three illustrated) may allow the communicative coupling of plug-in boards 364a, 364b (collectively 364, only two illustrated) to the processor system 304. There may, for example be one plug-in board 362 for each antenna 366a, 366b (collectively 366, only two illustrated, each of the antennas 366 and plug-in boards 364 constituting a separate channel. The slot connectors 362 may allow expansion or use with different antenna configurations. The plug-in boards 364 may each carry one or more circuits (e.g., analog and/or digital circuit components) configured to transmit interrogation signals from the respective antenna 366 and to monitor the antenna 366 for responses to the interrogation signals. For example, the plug-in boards 364 may implement or carry the circuits disclosed in U.S. patent application Ser. No. 11/759, 141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which patent applications are incorporated herein by reference in their entirety. processor system 304 may automatically recognize and be configured in response to a plug-in board 364 being coupled to an interface or slot connector 362, for example in a fashion similar to the coupling of a USB device to a computer system.

The processor system 304 may include one or more synchronization circuits or logic (not shown) configured to control and synchronize the operation of the various plug-in boards 364. The synchronization circuit or logic may be configured to cause one of the plug-in boards 364 to transmit an interrogation signal from a first antenna, and cause one or more of the other plug-in boards 364 to monitor for a response by a transponder to the interrogation signal. For instance, the synchronization circuit or logic may cause the plug-in boards 364 to monitor all of the antennas 366 for a response to the interrogation signal. Alternatively, the synchronization circuit or logic may cause the plug-in boards 364 to have all of the antennas 366 other than the antenna that transmitted a most recent interrogation signal monitor for a response. Such may advantageously allow monitoring sooner than would otherwise be possible since such can avoid the need to allow the transmitting antenna to return to a quiescent state after transmitting before monitoring for a response. The synchronization circuit or logic may synchronize the plug-in boards 364 to successively cause the various antennas to transmit, for example starting with an antenna at one end, and successively transmitting from each of the antennas in a defined order. As a further alternative, the synchronization circuit or logic may synchronize the plug-in boards 364 to cause the transmission of interrogations signals from a subset of the total set of antennas. While illustrated as removably coupled to the processor system 304, the plug-in boards 364 could be an integral unitary part thereof. For example, the various antennas may be controlled by respective circuits integrated into a signal circuit board. Alternatively, the various antennas may be controlled by a single circuit.

In a networked environment, program modules, application programs, or data, or portions thereof, can be stored in a server computing system (not shown). Those skilled in the relevant art will recognize that the network connections shown in FIG. 3 are only some examples of ways of establishing communications between computers, and other connections may be used, including wirelessly.

For convenience, the processor 306, system memory 308, network port 356, interface 346, interfaces or ports 358 and connector slots 362 are illustrated as communicatively coupled to each other via the system bus 310, thereby providing connectivity between the above-described components. In alternative embodiments of the processor system 304, the above-described components may be communicatively coupled in a different manner than illustrated in FIG. 3. For example, one or more of the above-described components may be directly coupled to other components, or may be coupled to each other, via intermediary components (not shown). In some embodiments, system bus 310 is omitted and the components are coupled directly to each other using suitable connections.

FIGS. 4 and 5 show a mat 400 that houses at least one antenna 402 and RF shield 404, according to one illustrated embodiment. One or more mats 400 may be positioned on or in the tables or stands 16 (FIG. 1) to position antennas 402 to interrogate the associated sterile fields 30. Additionally, one or more mats 400 may be located in or on a receptacle, such as the waste receptacle 18, to interrogate the associated non-sterile field 32.

The mat 400 may take a variety of forms, and may be disposable, or may be capable of withstanding multiple cycles of sterilization (e.g., chemical, heat, radiation, etc.). The mat 400 or portions thereof may be electrically insulative. The mat 400 may be radiolucent, particular if the mat is expected to be located between a patient 14 (FIG. 1) and a radiological imaging source. The mat 400 may take a conventional form, for example cotton, open cell or a closed cell foam rubber, rubber or silicone, with or without a suitable cover. The mat 400 may optionally be detachably secured to the table or stand 16 (FIG. 1) via various fasteners, for instance ties, or hook and loop fastener commercially available under the trademark VELCRO®.

The antenna 402 may take a variety of forms, for instance a loop antenna, dipole antenna, slot antenna, etc. The antenna 402 may constitute an electrically conductive trace carried by the mat 400. For example, the antenna 402 may be carried on an outer surface of the mat 400 or carried in an interior of the mat 400, as illustrated in FIGS. 4 and 5. The antenna 402 may be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) to be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

The RF shield 404 may take a variety of forms, which provide directional RF shielding. For instance, the RF shield 404 may comprise an electrically conductive plate or wire mesh to form a partial Faraday cage. Such may be used to ensure that only selected areas are interrogated. For example, such can be employed to ensure that only sterile fields 30 associated with the tables or stands 16 (FIG. 1) on which the mats 400 are located are interrogated. Such may advantageously be employed to ensure that transponders 33 located in the body of the patient 14 are not interrogated or read. The RF shield 404 may be generally planar, or may have one or more raised portions, for example an upstanding peripheral lip or edge 406.

A wired connector 408 may provide communicative coupling with the antenna 402. The wire connector may have a standard interface (e.g., USB connector) to allow selective coupling and uncoupling to the console 200 (FIG. 2) via one of the ports 210. Appropriate instructions (e.g., software, firmware) may be loaded in response to the coupling of the antenna 402 to the console 200. For example, instructions may be loaded to the control subsystem 38 (FIG. 1) of the console 36.

FIG. 6 shows a mat 600 that houses at least one antenna 602, an RF shield 604, and an integral RFID reader 606, according to one illustrated embodiment. The mat 600 may be positioned to interrogate sterile and/or non-sterile fields 30, 32.

As with the embodiment of FIGS. 4 and 5, the mat 600, antenna 602 and RF shield 604 may take a variety of forms. The various aspects described in reference to FIGS. 4 and 5 may be incorporated in the embodiment of FIG. 6, but will not be repeated here in the interest of brevity.

The RFID reader 606 may take a variety of forms, but will typically include a transmitter 606a and/or receiver 606b, which may be formed as a transceiver. The transmitter 606a and/or receiver 606b are communicatively coupled to the antenna 602 by electrically conductive paths. The reader 606 may be configured to transmit interrogation signals and receive response signals. The RFID reader 606 may further be configured to decode information encoded in the response signals, for example unique identifiers that uniquely identify the transponders the emit, backscatter or transmit the response signals. Alternatively, the RFID reader 606 may send the response signals to the control subsystem 38 for decoding.

Appropriate instructions (e.g., software, firmware) may be loaded in response to the coupling of the antenna 602 to the console 200. For example, instructions may be loaded to the control subsystem 38 (FIG. 1) of the console 36. Alternatively, or additionally, instructions may be loaded to the reader 606 of the mat 600.

Figure 7:
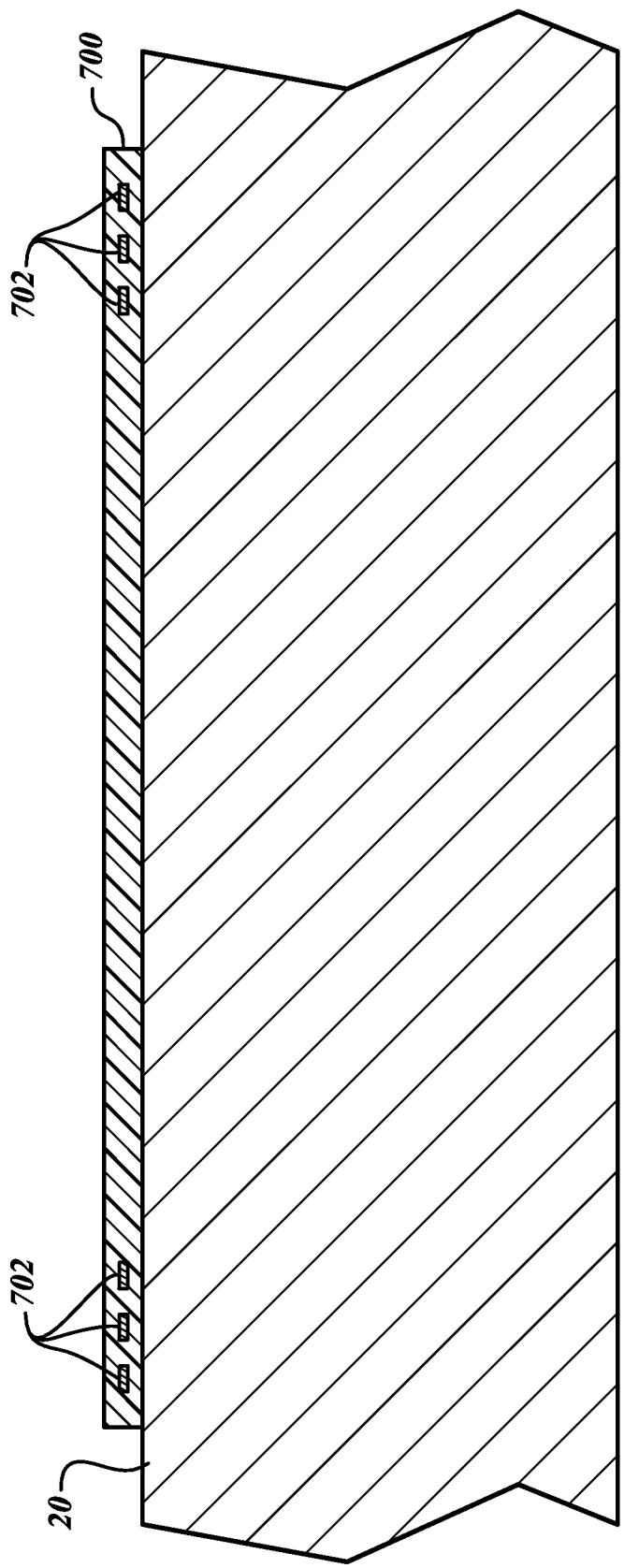
FIG. 7 is a cross-sectional view of a mat with at least one antenna, according to yet another illustrated embodiment, the mat carried by a patient support surface which comprise an RF shield.

FIG. 7 shows a mat 700 according to yet another illustrated embodiment, the mat 700 carried by a table or stand 20 (FIG. 1) which constitutes an RF shield.

The mat 700 includes one or more antennas 702. As in the previously described embodiments, the mat 700 may take a variety of forms, the various aspects of which will not be repeated here in the interest of brevity.

In contrast to the previously described embodiments In particular, the table or stand 20 or a portion thereof may consist of a metal such as a sheet of metal or mesh of metal wires, which functions as an RF or Faraday shield. The metal (e.g., stainless steel) may be on an outer surface of the table or stand 20, may be a layer in the table or stand 20 or may constitute the entire table or stand 20. Consequently, the mat 700 omits an RF shield.

FIGS. 8-10 show a tray 800 that includes at least one antenna 802 and an RF shield 804, according to one illustrated embodiment. One or more trays 800 may be positioned on one or more of the various tables or stands 20 (FIG. 1). Such may be in addition to, or in place of, mats 400, 600, 700 (FIGS. 4, 6 and 7, respectively). Such may be in addition to, or in place of antennas 40 integrated directly into the tables 20, for instance as illustrated in FIGS. 11-13.

As illustrated, the tray 800 has a receptacle 808 and at least one side wall 810 extending generally perpendicularly from surface 812. The antenna 802 may underlying the surface 812, or may be exposed either being deposited on the surface 812 or co-planar with the surface 812. One or more cables 814 and connectors 816 may provide communications and/or power between the antenna 802 and the control subsystem 38 (FIG. 1). As previously noted, the cable 814 and connector 816 may be a commercially available standard cable and connector, for instance a USB cable and connector. While not illustrated, a RFID reader may be integrated into the tray, for instance in a similar manner to that described above in reference to the mat 600 of FIG. 6.

Figure 11:
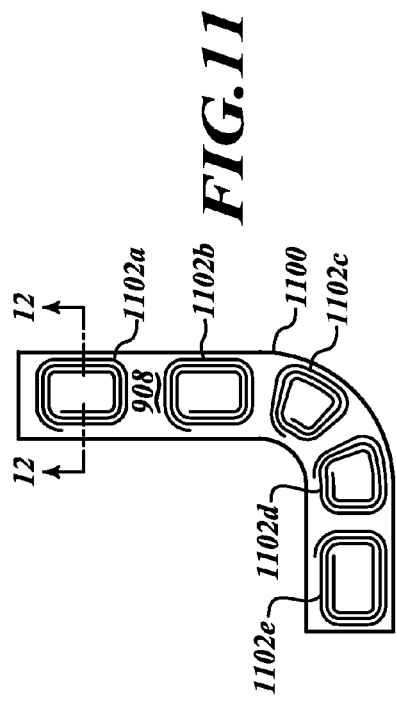
FIG. 11 is a top elevational view of an instrument or supply table with one or more antennas, according to one illustrated embodiment.
Figure 12:
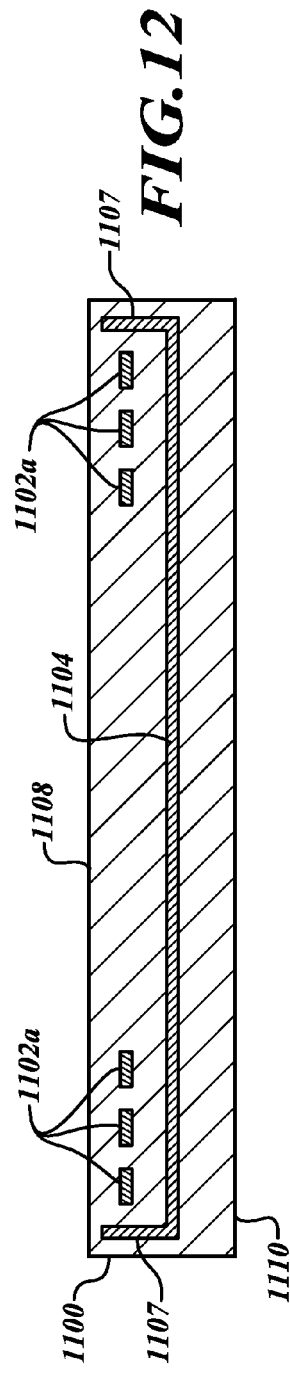
FIG. 12 is a cross-sectional view of the instrument or supply table of FIG. 11, taken along section line 12-12, showing an RF shield.
Figure 13:
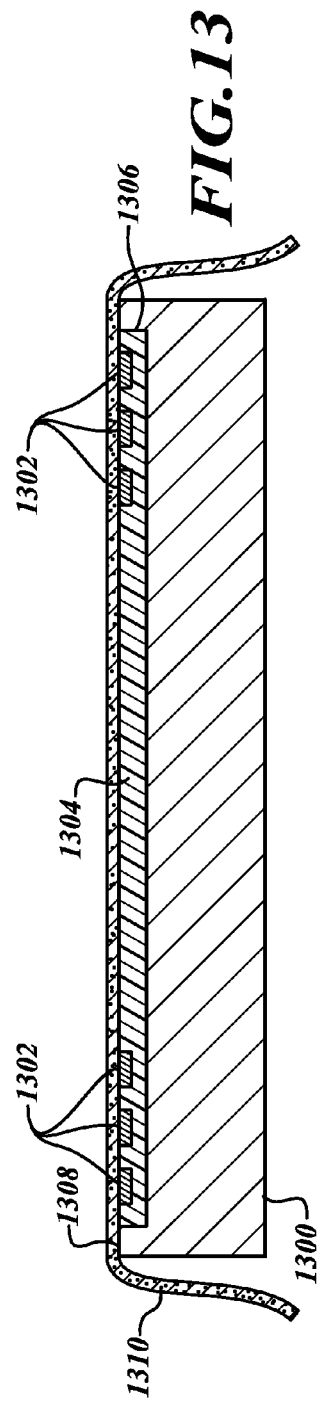
FIG. 13 is a cross-sectional view of the instrument or supply table with an antenna, according to another illustrated embodiment, the instrument or supply table comprising a material that acts as an RF shield.

FIGS. 11 and 12 show a table 1100 according to one illustrated embodiment, the table 1100 having one or more antennas 1102a-1102 (collectively 1102) integrated therein. The table 1100 may constitute an instrument table, supply table, Mayo table or stand, or back table, such as those illustrated in FIG. 1. Additionally, or alternatively, the table 1100 may constitute an operating table or other patient support structure or surface, such as those illustrated in FIG. 1.

The table 1100 may take a variety of forms, having any variety of shapes and employing any variety of materials. The materials may be capable of withstanding multiple cycles of sterilization (e.g., chemical, heat, radiation, etc.).

In some embodiments, that table 1100 or portions thereof may be made of electrically insulative materials, for example various resinous materials or plastics. Such may facilitate the integration of one or more antennas 1102 into the table 1100.

In such embodiments, the table may include an RF shield 1104. The RF shield 1104 may take the form of one or more metal sheets and/or metal wire, for instance a metal mesh. The RF shield 1104 may be generally planar, or may have one or more raised portions, for example an upstanding peripheral lip or edge 1107. Such may provide further directionality to the RF shielding function. The RF shield 1104 is positioned between a working surface 1108 of the table 1100 and where a patient 14 (FIG. 1) will be located when the table 1100 is in use. Such prevents the antenna(s) 1102 from detecting transponders in a body of a patient 14. While the antennas 1102 are illustrated as within the table 1100, in some embodiments that antennas 1102, or portions thereof, may be carried on an outer surface of the table 1100, for example on the working surface 1108. While the RF shield 1104 is illustrated as within the table 1100, in some embodiments that RF shield 1104, or portions thereof, may be carried on an outer surface of the table 1100, for example on a bottom surface 1110 thereof.

In some embodiments, that table 1100 or portions thereof may be made of electrically conductive materials, such as metals, for instance stainless steel. As explained in detail with reference to FIG. 13, such embodiments will typically require some electrically insulative material or structure be employed to prevent the antennas 1102 from electrically shorting.

FIG. 13 shows a table 1300 according to another illustrated embodiment, the table having one or more integral antennas 1302.

As discussed above, the table 1300 may take a variety of forms, having any variety of shapes and employing any variety of materials. The materials may be capable of withstanding multiple cycles of sterilization (e.g., chemical, heat, radiation, etc.). Aspects similar or identical to those of the embodiment of FIGS. 11 and 12 will not be repeated here in the interest of brevity.

As illustrated, the table 1300 is principally composed of an electrically conductive material, for example a metal, such as stainless steel. As noted above, such will typically require some electrically insulative material or structure be employed to prevent the antennas 1302 from electrically shorting. For example, the antennas 1302 may be formed as electrically conductive traces on a printed circuit board 1304 (e.g., layers of FR4, Kapton or the like), and integrated within or on a surface of the table 1300. For example, one or more circuit boards 1304 which carry the antennas 1302 may be received in one or more recesses 1306 formed in a working surface 1308 of the table 1300. An upper surface of the circuit board 1304 and antennas 1302 may be planar with the working surface 1308 of the table 1300. Since the table is composed of metal, the table functions as an RF shield. A sterile drape or cover 1310 may cover the working surface 1308, the antennas 1302, the circuit board 1304, and/or other portions of the table 1300.

Figure 14:
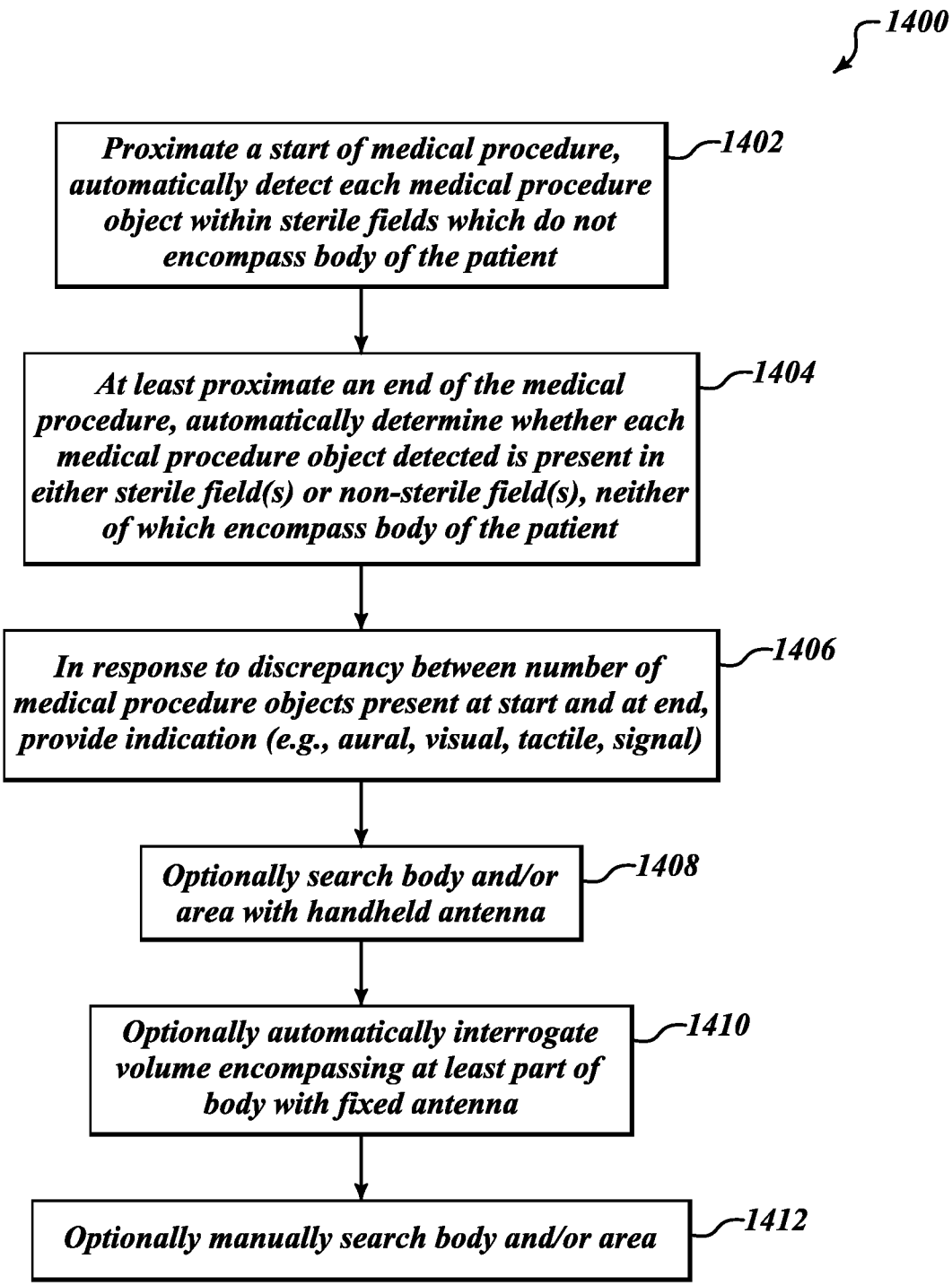
FIG. 14 is a high level flow diagram of a method of operating a system to track or monitor medical procedure instruments and supplies, according to one illustrated embodiment.

FIG. 14 shows a high level method 1400 of operating a medical procedure object accounting system to account for, track or monitor medical procedure instruments and supplies, according to one illustrated embodiment.

At 1402, at least proximate a start of a medical procedure on a patient, the medical procedure object accounting system (e.g., 34, FIG. 1) automatically detects each of a number of medical procedure objects for performing the medical procedure within at least one sterile field which at least one sterile field is at least proximate to the patient but which at least one sterile filed does not encompass any portion of a body of the patient.

At 1404, at least proximate an end of the medical procedure on the patient, the medical procedure object accounting system automatically determines whether each of the number of medical procedure objects detected within the at least one sterile field at least proximate the start of the medical procedure are present in at least one of either the at least one sterile field or at least one non-sterile field, neither of which the at least one sterile field or the at least one non-sterile field encompass any portion of the body of the patient.

At 1406, in response to determining that a discrepancy exists between the number of medical procedure objects present in the at least one sterile field at least proximate the start of the medical procedure and the number of medical procedure objects present in the at least one sterile field or the at least one non-sterile field at least proximate the end of the medical procedure, the medical procedure object accounting system provides an indication indicative of the existence of the discrepancy. Providing an indication indicative of the existence of the discrepancy may include at least one of providing an aural indication, providing a visual indication or providing a tactile indication.

If one or more medical procedure objects are not accounted for at the end of a medical procedure, certain acts may be taken prior to completion of the medical procedure.

For example, at 1408 the medical care providers may optionally automatically search a body cavity of the patient 14 and/or one or more areas of the medical procedure environment using the handheld antenna 44 (FIG. 1). Such may not only determine the presence/absence of a transponder 33 physically associated with an otherwise unaccounted for medical procedure object 24, but may provide an indication of the location of the transponder 33 and medical procedure object 24. In particular, the medical procedure object accounting system 34 may generate a signal indicative of the presence of the transponder 33 in response to the handheld antenna 44 being moved such that the transponder 33 physically associated with the missing medical procedure object 24 comes within an interrogation range of the handheld antenna 44.

For example, at 1410 a body cavity of the patient 14 (FIG. 1) may optionally be automatically searched using the second plurality of antennas 42 carried by the patient support structure 12. Such may not only determine the presence/absence in the body of a transponder 33 physically associated with an otherwise unaccounted for medical procedure object 24, but may provide an indication of the location of the transponder 33 and medical procedure object 24. In particular, the medical procedure object accounting system 34 may generate a signal indicative of the presence of the transponder 33. The medical procedure object accounting system 34 may generate a signal indicative of an approximate location of the transponder 33 in the body 14, and hence the medical object 24, based the locations of the antennas 42 which receive responses to interrogation signals and the relative ranges of each antenna. The medical procedure object accounting system 34 may identify a location associated with an antenna 42 that receives the strongest response. Alternatively, the medical procedure object accounting system 34 may employ more sophisticated approaches, such as triangulation between multiple antennas 42 to more accurately identify the location of the missing medical procedure object 24 and associated transponder 33.

Alternatively, or additionally, at 1412 the medical care providers may optionally manually search body cavity of the patient 14 (FIG. 1) for the missing medical procedure object(s). Likewise, the medical care providers may manually search one or more areas of the medical procedure environment 10 (FIG. 1) for the missing medical procedure object(s), for example one or more sterile or non-sterile areas, or areas that are not within the interrogation range of the medical procedure object accounting system 34.

Figure 15:
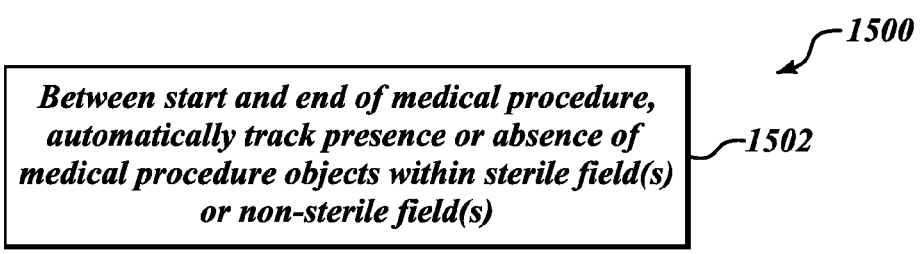
FIG. 15 is a high level flow diagram of a method of operating a system to track or monitor medical procedure instruments and supplies, according to another illustrated embodiment, the method useful with the method of FIG. 14.

FIG. 15 shows a high level method 1500 of operating a medical procedure object accounting system to account for, track or monitor medical procedure instruments and supplies, according to another illustrated embodiment, the method useful with the method of FIG. 14.

At 1502, between the start and the end of the medical procedure on the patient, the medical procedure object accounting system automatically tracks the presence or an absence of each of the number of medical procedure object within the at least one sterile field or the at least one non-sterile field.

Figure 16:
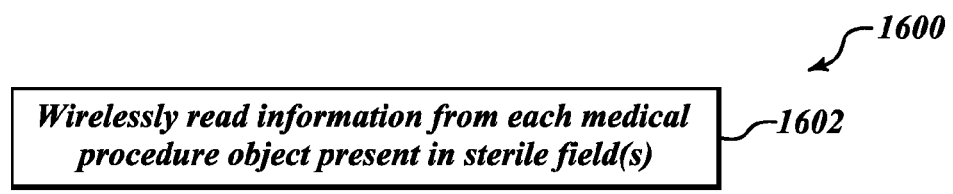
FIG. 16 is a flow diagram of a method of operating a system to track or monitor medical procedure instruments and supplies, according to another illustrated embodiment, the method useful with the method of FIG. 14.

FIG. 16 shows a method 1600 of operating a medical object accounting system to account for, track or monitor medical procedure instruments and supplies, according to another illustrated embodiment, the method useful with the method of FIG. 14.

At 1602, the medical procedure object accounting system automatically detects each of a number of medical procedure objects within at least one sterile field by wirelessly reading information from each of the medical procedure objects present in the at least one sterile field.

Figure 17:
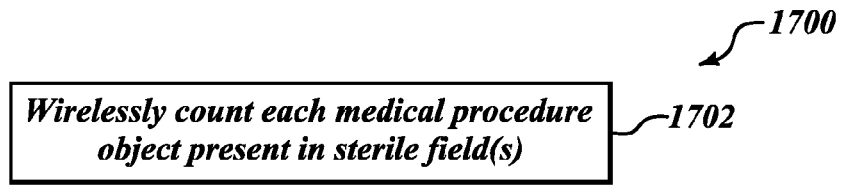
FIG. 17 is a flow diagram of a method of operating a system to track or monitor medical procedure instruments and supplies, according to another illustrated embodiment, the method useful with the method of FIG. 14.

FIG. 17 shows a method 1700 of operating a medical object accounting system to account for, track or monitor medical procedure instruments and supplies, according to another illustrated embodiment, the method useful with the method of FIG. 14.

At 1702, the medical procedure object accounting system automatically detects each of a number of medical procedure objects within at least one sterile field by wirelessly counting each of the medical procedure objects present in the at least one sterile field.

Figure 18:
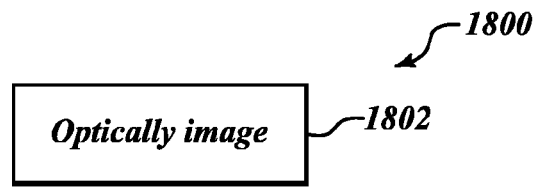
FIG. 18 is a flow diagram of a method of reading information for use in operating a system to track or monitor medical procedure instruments and supplies, according to one illustrated embodiment.

FIG. 18 shows a method 1800 of reading information for use in operating a medical object accounting system to account for, track or monitor medical procedure instruments and supplies, according to one illustrated embodiment.

At 1802, the medical procedure object accounting system wirelessly reads or wirelessly counts by optically imaging the sterile field(s). For example, the medical procedure object accounting system or a machine-readable symbol imager associated therewith may optically image a respective machine-readable symbol carried by each instrument or supply in the sterile field.

Figure 19:
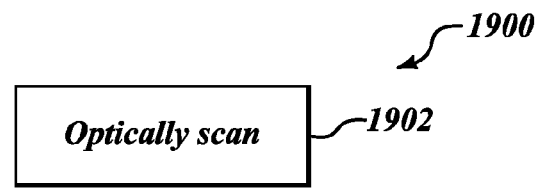
FIG. 19 is a flow diagram of a method of reading information for use in operating a system to track or monitor medical procedure instruments and supplies, according to another illustrated embodiment.

FIG. 19 shows a method 1900 of reading information for use in operating a medical object accounting system to account for, track or monitor medical procedure instruments and supplies, according to another illustrated embodiment.

At 1902, the medical procedure object accounting system wirelessly reads or wirelessly counts by optically scanning the sterile field. For example, the medical procedure object accounting system or a machine-readable symbol scanner associated therewith may optically scan a respective machine-readable symbol carried by each instrument or supply in the sterile field.

Figure 20:
FIG. 20 is a flow diagram of a method of a method of reading information for use in operating a system to track or monitor medical procedure instruments and supplies, according to yet another illustrated embodiment.

FIG. 20 shows a method 2000 of a method of reading information for use in operating a medical object accounting system to account for, track or monitor medical procedure instruments and supplies, according to yet another illustrated embodiment.

At 2002, the medical procedure object accounting system wirelessly reads or wirelessly counts by wirelessly interrogating in the sterile field(s). For example, the medical procedure object accounting system or RFID interrogator associated therewith may transmit interrogation signals within the sterile field(s) and receive response signals from RFID transponders physically associated with respective ones of the instruments and/or supplies in the sterile field(s).

Figure 21:
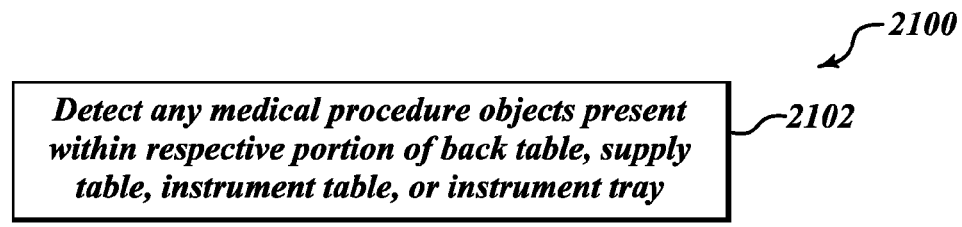
FIG. 21 is a flow diagram of a method of operating a system to track or monitor medical procedure instruments and supplies, according to one illustrated embodiment, useful in the method of FIG. 14.

FIG. 21 shows a method 2100 of operating a medical procedure accounting system to account for, track or monitor medical procedure instruments and supplies, according to one illustrated embodiment, useful in the method of FIG. 14.

At 2102, the medical procedure object accounting system detects any medical procedure objects present within a respective portion of an instrument table, supply table, Mayo table or stand, or back table. For example, the medical procedure object accounting system may transmit interrogation signals from a number of antennas positioned to interrogate transponders that are within the area or volume encompassed by the tables. The medical procedure object accounting system may receive response signals produced in response to the interrogation signals by any transponders that are present.

Alternatively, or additionally, a handheld RFID reader may be used to interrogate the areas of the respective tables, or a machine-readable symbol reader may be employed to read machine-readable symbols physically associated with instruments and/or supplies on the tables.

Figure 22:
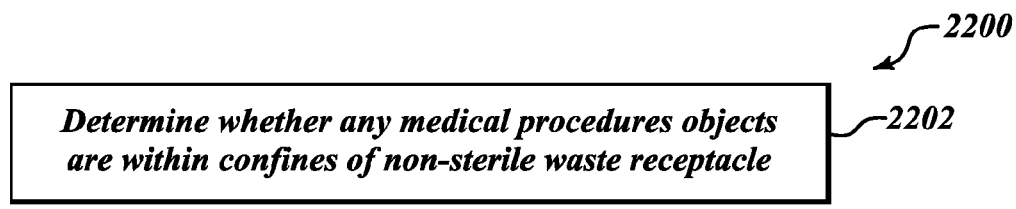
FIG. 22 is a flow diagram of a method of operating a system to track or monitor medical procedure instruments and supplies, according to another illustrated embodiment, useful in the method of FIG. 14.

FIG. 22 shows a method 2200 of operating a medical procedure accounting system to account for, track or monitor medical procedure instruments and supplies, according to another illustrated embodiment, useful in the method of FIG. 14.

At 2202, the medical procedure object accounting system wherein automatically determines whether each of the number of medical procedure objects detected within the at least one sterile field at least proximate the start of the medical procedure are present in at least one of either the at least one sterile field or at least one non-sterile field by determining whether any of the medical procedures objects are within a respective confines of a waste receptacle. For example, the medical procedure accounting system or RFID reader associated therewith may transmit one or more interrogation signals in a volume encompassed by the waste receptacle and detect and responses to the interrogation signals. Alternatively, a machine-readable symbol reader may read any machine-readable symbols associated with instruments or supplies as such are introduced into the waste receptacle.

Figure 23:
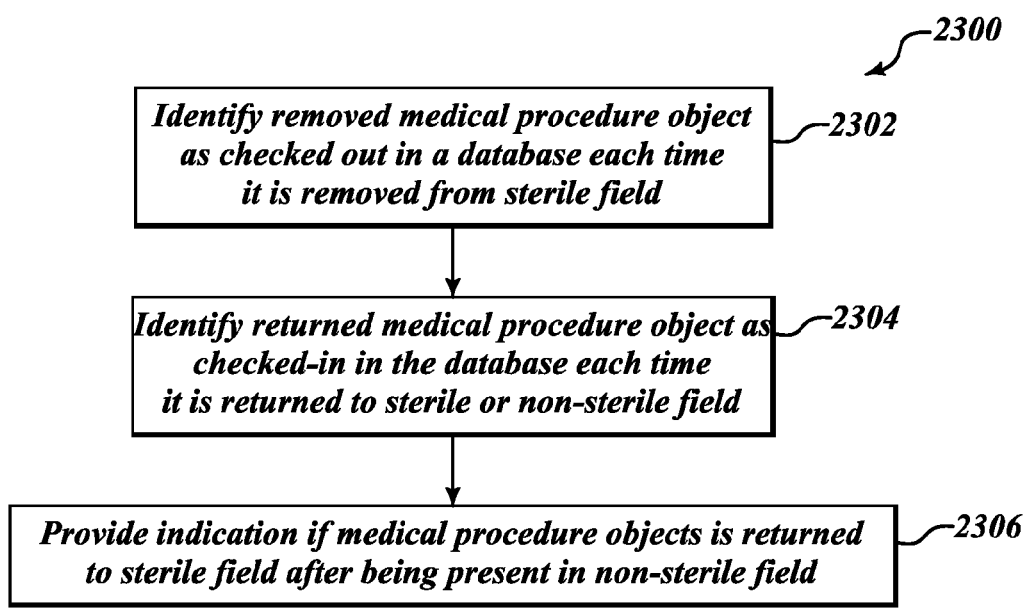
FIG. 23 is a high level flow diagram of a method of operating a system to track or monitor medical procedure instruments and supplies, according to another illustrated embodiment.

FIG. 23 shows a high level method 2300 of operating an accounting system to account for, track or monitor medical procedure instruments and supplies, according to another illustrated embodiment.

At 2302, the medical procedure accounting system identifies medical procedure objects removed from a sterile field as checked out in a database each time the medical procedure object is removed from sterile field. For example, the medical procedure object accounting system may update a field of a record associated or corresponding to the particular instrument, supply or transponder physically associated therewith.

At 2304, the medical procedure accounting system identifies medical procedure objects returned to a sterile field or a non-sterile field as checked-in in the database each time the medical procedure object is returned to sterile or non-sterile field. For example, the medical procedure object accounting system may update a field of a record associated or corresponding to the particular instrument, supply or transponder physically associated therewith.

At 2306, the medical procedure accounting system provides an indication if a medical procedure object is returned to sterile field after being present in non-sterile field. For example, the medical procedure object accounting system may produce a visual alert or notification, an aural alert or notification, and/or a tactile alert or notification.

Figure 24:
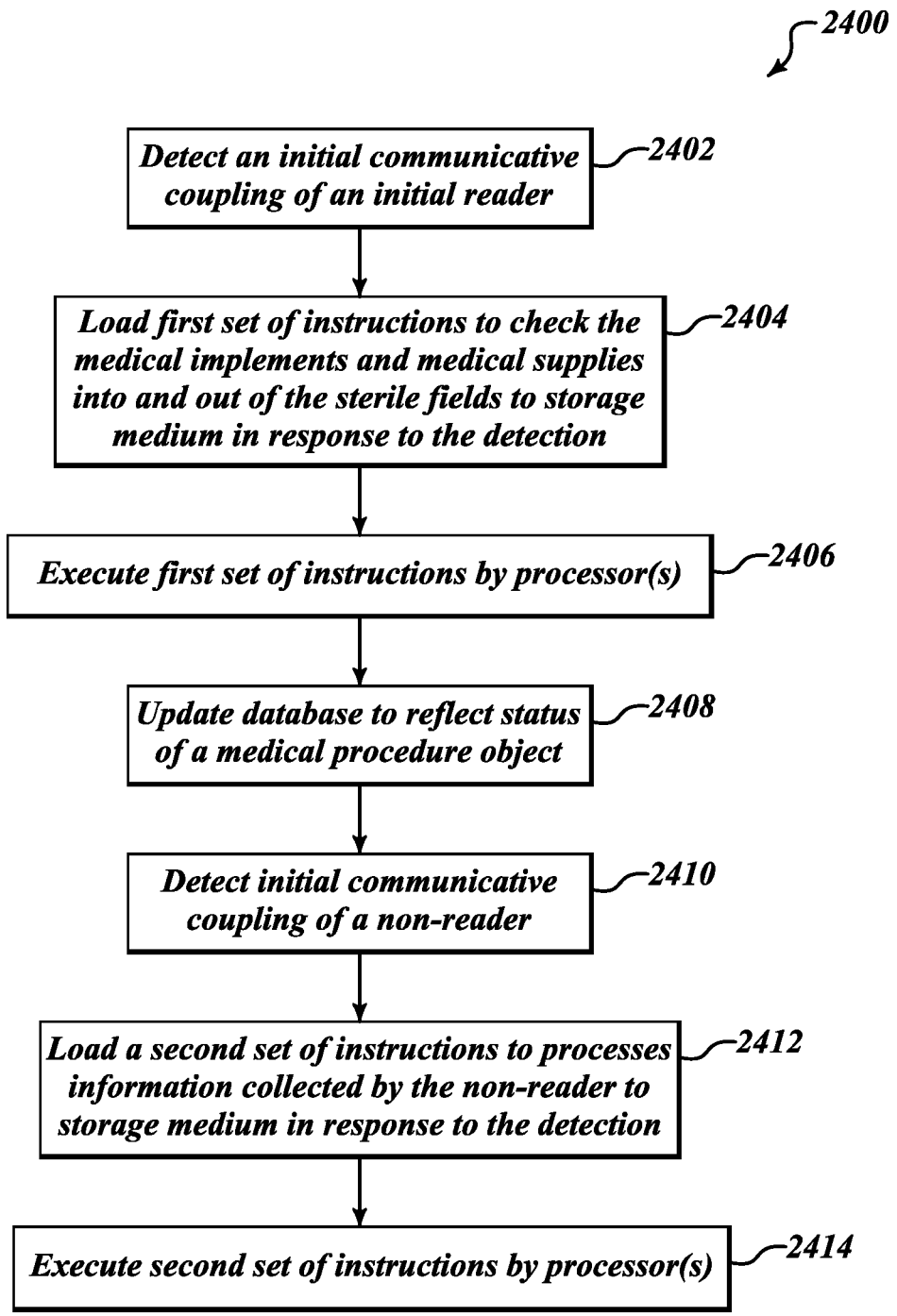
FIG. 24 is a high level flow diagram of a method of operating a system that tracks or monitors medical procedure instruments and supplies as well as operating with peripheral non-reader equipment, according to one illustrated embodiment.

FIG. 24 shows a high level a method 2400 of operating an accounting system that accounts for, tracks or monitors medical procedure instruments and supplies as well as operating with peripheral non-reader equipment, according to one illustrated embodiment.

At 2402, the medical procedure accounting system detects an initial communicative coupling of an reader. The reader may, for example, take the form of a machine-readable symbol reader or an RFID reader. The communicative coupling may, for example, take the form of the connection of a USB connector or other connector to a corresponding USB port or other port on a console. Initial refers to the first time a reader requiring a specific set of instructions is communicatively coupled to the medical procedure accounting system. Thus, the coupling of a reader from a different manufacturer or a different model or version than other readers already communicatively coupled is recognized as an initial coupling requiring loading of a respective set of instructions.

At 2404, the medical procedure accounting system loads a first set of instructions to at least one computer- or processor-readable storage medium in response to the detection of the initial communicative coupling of the reader. The first set of instructions may configure the reader to operate with the medical procedure accounting system to check the medical implements and medical supplies into and out of the sterile fields. Additionally, or alternatively, the first set of instructions may configure the medical procedure accounting system to operate with the reader, for example recognizing a specific format in which the reader provides information or data.

At 2406, the reader and/or medical procedure accounting system executes the first set of instructions by processor(s). As noted above, the first set of instructions may configure the reader to operate with the medical procedure accounting system and/or configures the medical procedure accounting system to work with the reader. Thus true "plug and play" functionality may be achieved, allowing various readers to be added to the system with automatic configuration.

At 2408, the medical procedure accounting system updates a database to reflect status of the medical procedure object(s).

At 2410, the medical procedure accounting system detects an initial communicative coupling of a non-reader. The non-reader may, for example, take the form of a dedicated piece of medical procedure related equipment. For instance the medical procedure related equipment may take the form of anesthetizing equipment 20b, heart/lung machines, cauterization equipment, defibrillator 20c, aspirator equipment, infusion pump, dialysis machine, intra-aortic balloon pump, various monitors such as blood pressure, heart or pulse rate, pulse-oxygen (pulse-ox or pulse oximetry) sensor 20d, temperature, EKG sensors or electrodes, intra-cranial pressure sensors, other dedicated medical diagnostic, therapeutic or monitoring equipment, etc. The communicative coupling may, for example, take the form of the connection of a USB connector or other connector to a corresponding USB port or other port on a console. Initial refers to the first time a non-reader device requiring a specific set of instructions is communicatively coupled to the medical procedure accounting system. Thus, the coupling of a non-reader device from a different manufacturer or a different model or version than other non-reader devices already communicatively coupled is recognized as an initial coupling requiring loading of a respective set of instructions.

At 2412, the medical procedure accounting system loads a second set of instructions to at least one computer- or processor-readable storage medium in response to the detection of the initial communicative coupling of the non-reader. The second set of instructions may configure the non-reader device to processes information collected by the non-reader in order to operate with the medical procedure accounting system to check the medical implements and medical supplies into and out of the sterile fields. Additionally, or alternatively, the second set of instructions may configure the medical procedure accounting system to operate with the non-reader device, for example recognizing a specific format in which the non-reader device provides information or data and/or to provide operational instructions to the non-reader device.

At 2414, the medical procedure accounting system executes the second set of instructions by processor(s). As noted above, the second set of instructions may configure the non-reader to operate with the medical procedure accounting system and/or configure the medical procedure accounting system to operate with the non-reader device. Thus true "plug and play" functionality may be achieved, allowing various medical equipment to be added to the system with automatic configuration.

Transponders useful for marking medical procedure related objects may take a variety of form. Transponders capable of withstanding sterilization procedures would be particularly advantageous. A permanent memory type transponder which retains information or data, for instance a unique identifier and which is substantially gamma ray resistant and capable of being subjected to the relatively high temperatures often associated with sterilization may be formed from an antenna, passive power or backscatter circuit and a permanent memory circuit communicatively coupled to the antenna and powered via the passive power or backscatter circuit to transmit the contents of the permanent memory in response to power derived from an interrogation signal. The permanent memory circuit may advantageously take the form or may incorporate aspects of the permanent memory circuits described in one or more of U.S. Pat. Nos. 7,609,538; 7,471,541; 7,269,047; 7,042,722; 7,031,209; 6,992,925; 6,972,986; 6,956,258; 6,940,751; 6,898,116; 6,856,540; 6,822,888; 6,798,693; 6,791,891; 6,777,757; 6,766,960; 6,700,151; 6,671,040; 6,667,902; and 6,650,143, all of which are incorporated herein by reference in their entireties to the extent that such are not inconsistent with the other portions of present detailed description. Applicants have recognized that such permanent memory circuits may be resistant to gamma ray radiation and high temperatures, and thus may be particularly suitable for use in manufacturing transponders for use in marking objects that will be subjected to the extremes of sterilization. The permanent memory type transponder may include a housing, shell or encapsulant. Such a permanent memory transponder may be particularly useful for marking gauze or sponges. Such a transponder may be attached to a medical procedure related object in any variety of fashions, including sewn to, sewn in, adhered via adhesives or heat or RF welding, riveted, tied to, via a snap, stapled, etc.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For instance, the teachings herein may employ any variety of other electrodes, sensors or transducers and diagnostic, therapeutic or monitoring equipment. For example, photo-electric pulse plethysmograph transducers, respiratory effort transducers, GSR finger electrode transducers, physiological sounds microphone, active electrodes, air flow transducers, blood pressure transducers, blood pressure cuff transducers, hand dynamometers, variable range force transducer, twin axis goniometer, torsion meter, laser Doppler surface flow probe, skin surface temperature, fast response temperature probe, surface temperature banjo probe, liquid immersion probe, digit surface temperature probe, accelerometer, pulse oximeters transducer.

Also for instance, many of the embodiments described herein, perform interrogation and detection of transponder tagged objects using multiple antennas. Successive ones of the antennas may be used to transmit an interrogation signal, while two or more antennas are monitored for a response to the interrogation signal. Such may provide significant advantages over more conventional methods, for example motion based methods that employ motion (e.g., sweeping) of an antenna (e.g., wand) over a patient. For instance, this allows the transmit and receive paths to the transponder to be different from one another (e.g., transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the $6^{th}$ root of the input power. However, when using multiple antennas to transmit and receive over the same area, interrogation path length in one direction may be shorter. Another advantage is that all scan time may be averaged, allowing a longer noise time averaging (e.g., 10 seconds) as opposed to motion based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

In some embodiments, a high speed LINUX based microprocessor may be employed in the console. In some embodiments, an LCD touch screen may be employed as a user interface device. Some embodiments may include update ready software images for new applications. Such may facilitate the automatic loading of instructions on detection of a new device. RF reading may be performed using a handheld wand, via antennas located at the various nursing stations, a standalone handheld RFID reader, and/or via antennas positioned to interrogate all or part of a body. A PDR log may be maintained. Information may be offloaded in a variety of fashions, for instance a memory stick, wireless data transfer, or printer. An optional monitor may be coupled to the console to display video or other images. In some embodiment, one or more machine-readable symbol readers may be coupled to the console to read machine-readable symbols and transfer read data to the console. In some embodiments, a reading or scanning device (e.g., handheld antenna, handheld RFID reader, machine-readable symbol readers, antenna position to reader items on various tables and stands or nursing stations) may be a USB device, which automatically uploads counting or accounting instructions (e.g., software) to a console when communicatively coupled thereto. The reading or scanning device may be appropriate for use with aseptic techniques, for example via placement under a drape or otherwise covered, or having been sterilized (e.g., autoclave). The reader or scanning device may be an antenna suitable for interrogating RFID transponders or a reader suitable for interrogating RFID transponders. Such may be incorporated in a mat, dish, tray or packed coil apparatus. Such may be used as a check in and/check out apparatus to ensure management or accounting of objects in the medical procedure environment. A suitable antenna may be a coil that enables object reading in random orientations over specific portions of nurse management areas (e.g., instrument or supply tables or stands).

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Patent Publication No. 2004/0250819, published Dec. 16, 2004; U.S. Provisional Patent Application No. 60/811,376 filed Jun. 6, 2006; U.S. Provisional Patent Application No. 61/109,104 filed Oct. 28, 2008; U.S. Provisional Patent Application No. 61/222,443 filed Jul. 1, 2009; U.S. Provisional Patent Application No. 61/222,847 filed Jul. 2, 2009; U.S. Provisional Patent Application No. 61/242,704, filed Sep. 15, 2009; U.S. Provisional patent application Ser. No. 61/242,699 filed Sep. 15, 2009; U.S. Non-Provisional patent application Ser. No. 11/743,104 filed May 1, 2007; U.S. Non-Provisional patent application Ser. No. 12/472,199 filed May 26, 2009; U.S. Non-Provisional patent application Ser. No. 12/473,059 filed May 27, 2009; U.S. Non-Provisional Patent Application No. 12/606,686, filed Oct. 27, 2009; U.S. Non-Provisional patent application Ser. No. 12/606,688 filed Oct. 27, 2009; U.S. Non-Provisional patent application Ser. No. 12/606,963 filed Oct. 27, 2009; and U.S. Pat. No. 6,026,818, issued Feb. 22, 2000, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of accounting for medical procedure objects, the method comprising:
    at least proximate a start of a medical procedure on a patient, automatically detecting each of a number of medical procedure objects for performing the medical procedure within at least one sterile field using at least one sterile field antenna that is carried by at least a portion of a surface proximate the at least one sterile field, fixed with respect to the at least one sterile field, and having a detection range coextensive with the at least one sterile field, and which at least one sterile field is at least proximate to the patient but which at least one sterile field does not encompass any portion of a body of the patient;
    each time one of the medical procedure objects is removed from the at least one sterile field, identifying the removed medical procedure object as checked out in a database; and
    each time the medical procedure object is returned to the at least one sterile field or to a non-sterile field, identifying the returned medical procedure object as checked-in in the database;
    automatically detecting a first medical procedure object of the number of medical procedure objects within the non-sterile field using at least one non-sterile field antenna that is carried proximate the non-sterile field and that has a detection range coextensive with the non-sterile field, wherein the non-sterile field does not encompass any portion of the body of the patient;
    after detecting the first medical procedure object within the non-sterile field, automatically detecting the first medical procedure object within the at least one sterile field using the at least one sterile field antenna;
    in response to detecting the first medical procedure object within the at least one sterile field after detecting the first medical procedure object within the non-sterile field, providing an indication that the first medical procedure object has been returned to the at least one sterile field after being present in the non-sterile field; and
    at least proximate an end of the medical procedure on the patient, automatically determining whether each of the number of medical procedure objects detected within the at least one sterile field at least proximate the start of the medical procedure are present in at least one of either the at least one sterile field or at least one non-sterile field, neither of which the at least one sterile field and the at least one non-sterile field encompass any portion of the body of the patient.

2. The method of claim 1, further comprising:
    in response to determining that a discrepancy exists between the number of medical procedure objects present in the at least one sterile field at least proximate the start of the medical procedure and the number of medical procedure objects present in the at least one sterile field or the at least one non-sterile field at least proximate the end of the medical procedure, providing an indication indicative of the existence of the discrepancy.

3. The method of claim 2 wherein providing an indication indicative of the existence of the discrepancy includes at least one of providing an aural indication, providing a visual indication or providing a tactile indication.

4. The method of claim 1 wherein automatically detecting each of a number of medical procedure objects within at least one sterile field includes at least one of wirelessly reading information from each of the medical procedure objects present in the at least one sterile field or wirelessly counting each of the medical procedure objects present in the at least one sterile field, and wherein wirelessly reading or wirelessly counting includes at least one of optically imaging, optically scanning, or wirelessly interrogating at least one of the medical procedure objects or a number of transponders associated with the medical procedure objects.

5. The method of claim 1 wherein the at least one sterile field is respectively coextensive with at least a portion of at least one of a back table, a supply table, or an instrument table, and wherein automatically detecting each of a number of medical procedure objects within at least one sterile field includes detecting any of the medical procedure objects present within respective portion of the back table, the supply table, or the instrument table.

6. The method of claim 1 wherein the at least one sterile field is respectively coextensive with an outer perimeter of an instrument tray, and wherein automatically detecting each of a number of medical procedure objects within at least one sterile field includes detecting any of the medical procedure objects present within the outer perimeter of the instrument tray.

7. The method of claim 1 wherein the at least one non-sterile field includes a waste receptacle and wherein automatically determining whether each of the number of medical procedure objects detected within the at least one sterile field at least proximate the start of the medical procedure are present in at least one of either the at least one sterile field or at least one non-sterile field includes determining whether any of the medical procedures objects are within a respective confines of the waste receptacle.

8. The method of claim 1, further comprising:
between the start and the end of the medical procedure on the patient, automatically tracking the presence or an absence of each of the number of medical procedure object within the at least one sterile field or the at least one non-sterile field.

9. The method of claim 1 wherein automatically detecting each of a number of medical procedure objects for performing the medical procedure within at least one sterile field using at least one antenna that is carried by at least a portion of a surface proximate the at least one field includes:
automatically detecting each of a number of medical procedure objects for performing the medical procedure within at least one sterile field using at least one antenna that is carried by at least a portion of a surface that includes at least one of: at least a portion of a mat carrying the antenna placed beneath at least a portion of the one or more sterile fields; at least a portion of a tray carrying the antenna, the tray beneath at least a portion of the one or more sterile fields; or at least a portion of a surgical instrument support surface carrying the antenna, the surgical instrument support surface beneath at least a portion of the one or more sterile fields.

10. A system to account for medical procedure objects, the system comprising:
a plurality of sterile fields, each of the sterile fields encompassing an area that excludes any portion of a body of a patient on which a medical procedure is performed, each of the sterile fields including at least one sterile field antenna that is carried by at least a portion of a surface proximate the at least one sterile field, fixed with respect to the respective sterile field and having a detection range coextensive with the respective sterile field;
a non-sterile field that encompasses an area that excludes any portion of the body of the patient on which the medical procedure is performed, the non-sterile field including at least one non-sterile field antenna that is carried proximate the non-sterile field, fixed with respect to the non-sterile field, and having a detection range coextensive with the non-sterile filed;
a control subsystem including at least one processor and at least one processor-readable storage medium, the control subsystem configured to:
at least proximate a start of a medical procedure on a patient, use the respective sterile field antennas to automatically detect each of a number of medical procedure objects for performing the medical procedure within any of the plurality of sterile fields;
each time one of the medical procedure objects is removed from the at least one sterile field, identify the removed medical procedure object as checked out in a database; and
each time the medical procedure object is returned to the at least one sterile field or to the non-sterile field, identify the returned medical procedure object as checked-in in the database;
use the non-sterile field antenna to detect a first medical procedure object of the number of medical procedure objects within the non-sterile field;
after detection of the first medical procedure object within the non-sterile field, detect the first medical procedure object within at least one sterile field using the respective at least one sterile field antenna;
in response to detection of the first medical procedure object within the at least one sterile field after detection of the first medical procedure object within the non-sterile field, provide an indication that the first medical procedure object has been returned to the at least one sterile field after being present in the non-sterile field; and
at least proximate an end of the medical procedure on the patient, automatically determine whether each of the number of medical procedure objects detected within any of the sterile fields at least proximate the start of the medical procedure are present in at least one of either the sterile fields or at least one non-sterile field.

11. The system of claim 10, further comprising:
at least one receiver communicatively coupled to the at least one antenna in at least some of the plurality of sterile fields, the antennas and receiver providing a range that is about coextensive with the sterile fields and which range does not extend into any portion of the body of the patient when the patient is supported by a patient support structure during the medical procedure.

12. The system of claim 11, further comprising:
at least one transmitter communicatively coupled to the antennas to transmit an interrogation signal to any transponders in the sterile fields.

13. The system of claim 11 wherein the sterile fields are coextensive with at least a portion of a back table, a supply table, and an instrument table, respectively.

14. The system of claim 13 wherein one of the sterile fields is coextensive with a portable instrument tray and at least one of the antennas is physically coupled to the portable instrument tray.

15. The system of claim 11, further comprising:
a plurality of substrates, each of the substrates carrying at least a respective one of the antennas, the substrates positionable with respect to a respective one of each of the sterile fields such that a range of the at least respective one of the antennas covers the respective sterile field.

16. The system of claim 11 wherein the at least one receiver includes a plurality of receivers, each of at least some of the receivers physically coupled to a respective one of the substrates.

17. The system of claim 11 wherein the at least one receiver includes a plurality of receivers, each of at least some of the receivers physically housed in a controller console, at least some of the antennas remotely located from the control console and communicatively coupled to respective ones of the receivers via a respective wired connection.

18. The system of claim 10, further comprising:
at least one transmitter and receiver; and
at least one antenna that is a part of a handheld wand, the at least one antenna communicatively coupleable to the at least one transmitter and receiver to transmitting interrogation signals and receive response signals in a random orientation.

19. The system of claim 18 wherein the control subsystem is further configured to cause interrogations signals to be transmitted and to read identifiers encoded in response signals received from transponders in response to the interrogation signals.

20. The system of claim 10, further comprising:
a plurality of antennas communicatively coupled via at least one universal serial bus communications link to the control subsystem, at least some of the antennas located at least proximate respective ones of the sterile fields.

21. The system of claim 10 wherein the control subsystem is resident in a console and is configured by an application program loaded in response to communicative coupling of a reader to the console.

22. The system of claim 10, further comprising:
a plurality of readers communicatively coupled to the console and positioned at least proximate respective ones of the sterile fields and the non-sterile field, the readers including at least one of radio frequency identification readers or machine-readable symbol readers.

23. The system of claim 10, further comprising:
at least one cover sized to completely cover at least one of the antennas, the cover comprising a material that is capable of withstanding sterilization.

24. The system of claim 11 wherein the non-sterile field is coextensive with a waste receptacle.

25. A system to account for medical procedure objects, the system comprising:
a computer system including at least one processor and at least one computer-readable storage medium;
a number of readers to monitor a number of sterile fields in which at least one of medical implements or medical supplies are kept for use during medical procedures, and which any single one of the sterile fields does not encompass a patient support surface that supports a patient during a medical procedure, the readers selectively communicatively coupleable to the computer system;
a non-sterile field reader to monitor a non-sterile field in which at least one of the medical implements or the medical supplies are placed or disposed after use during medical procedures and which non-sterile field does not encompass a patient support surface that supports the patient during the medical procedure, that non-sterile field reader selectively communicatively coupleable to the computer system; and
a set of instructions executed by the at least one processor responsive to an initial communicative coupling of one of the readers to the computer system, the set of instructions to cause the computer system to:
autonomously identify the medical implements and medical supplies present in the number of sterile fields based at least in part on communication received from the number of readers;
each time one of the medical procedure objects is removed from the at least one sterile field, autonomously identify the removed medical procedure object as checked out in a database;
each time the medical procedure object is returned to the at least one sterile field or to the at least one non-sterile field, autonomously identify the returned medical procedure object as checked-in in the database;
autonomously detect a first medical implement or medical supply of the identified medical implements and medical supplies within the non-sterile field based at least in part on communications received from the non-sterile field reader;
after autonomous detection of the first medical procedure object within the non-sterile field, autonomously detect the first medical implement or medical supply within one of the number of sterile fields based at least in part on communications received from the respective reader; and
in response to autonomous detection of the first medical implement or medical supply within one of the number of sterile fields after autonomous detection of first medical implement or medical supply within the non-sterile field, provide an indication that the first medical implement or medical supply has been returned to the one of the number of sterile fields after being present in the non-sterile field.

26. The system of claim 25 wherein the readers each include a substrate that is positioned at least proximate at least one of a back table, a supply table, or an instrument table.

27. The system of claim 25 wherein the readers each include an antenna operable to transmit an interrogation signal to a respective one of the sterile fields and to receive a response signal from any transponders in the respective one of the sterile fields.

28. The system of claim 25 wherein the readers are communicatively coupled to the computer system by at least one wired or wireless universal serial bus.

29. A method of operating a medical procedure object accounting system, the method comprising:
detecting by a computer system an initial communicative coupling of an initial reader;
loading a first set of instructions to at least one computer-readable storage medium in response to the detection of an initial communicative coupling of the initial reader to the computer system, the instructions executable by at least one processor of the computer system to cause the computer system to:
autonomously identify medical implements and medical supplies present in a number of sterile fields that do not encompass any portion of a body of a patient;
each time one of the medical procedure objects is removed from the at least one sterile field, autonomously identifying the removed medical procedure object as checked out in a database;
each time the medical procedure object is returned to the at least one sterile field or to at least one non-sterile field, autonomously identifying the returned medical procedure object as checked-in in the database;
autonomously detect a first medical procedure object within a non-sterile field that dose not encompass any portion of the body of the patient;

after autonomous detection of the first medical procedure object within the non-sterile field, autonomously detect the first medical procedure object within one of the number of sterile fields; and in response to autonomous detection of the first medical procedure object within one of the number of sterile fields after autonomous detection of the first medical procedure object within the non-sterile field, provide an indication that the first medical procedure object has been returned to the one of the number of sterile fields after being present in the non-sterile field; and executing the first set of instructions by the at least one processor.

30. The method of claim 29 wherein executing the first set of instructions by the at least one processor causes the at least one processor to autonomously check the identified medical implements and medical supplies into and out of the sterile fields, by:

limiting a detection range of at least one antenna to be coextensive with at least one sterile field proximate a patient, but not encompass any portion of a body of the patient by directionally shielding via a radio frequency ("RF") shield, at least a portion of an electromagnetic emission from the at least one antenna, the at least one antenna carried by at least a portion of a surface proximate the at least one sterile field and fixed with respect to the at least one sterile field;

at least proximate a start of a medical procedure on a patient, automatically detecting any of the medical implements and medical supplies within the at least one sterile field; and at least proximate an end of the medical procedure on the patient, automatically determining whether each of the number of medical implements and medical supplies detected within the at least one sterile field at least proximate the start of the medical procedure are present in at least one of either the at least one sterile field or at least one non-sterile field, neither of which the at least one sterile field or the at least one non-sterile field encompass any portion of the body of the patient.

31. The method of claim 29 wherein executing the first set of instructions by the at least one processor causes the at least one processor to check the medical implements and medical supplies into and out of the sterile fields, by:

updating a database stored in the at least one computer-readable medium to reflect a status of a medical procedure object.

32. The method of claim 30, further comprising:

detecting by a computer system an initial communicative coupling of a non-reader;

loading a second set of instructions to at least one computer-readable storage medium in response to the detection of an initial communicative coupling of the non-reader to the computer system, the instructions executable by at least one processor of the computer system to cause the computer system to process information collected by the non-reader; and executing the second set of instructions by the at least one processor.

* * * * *